(12) United States Patent
Morishita

(10) Patent No.: US 11,015,046 B2
(45) Date of Patent: May 25, 2021

(54) THERMOPLASTIC RESIN COMPOSITION, HOT MELT ADHESIVE, AUTOMOBILE MEMBER, AND HYGIENIC MATERIAL MEMBER

(71) Applicant: KURARAY CO., LTD., Kurashiki (JP)

(72) Inventor: Yoshihiro Morishita, Kamisu (JP)

(73) Assignee: KURARAY CO., LTD., Kurashiki (JP)

( * ) Notice: Subject to any disclaimer, the term of this patent is extended or adjusted under 35 U.S.C. 154(b) by 0 days.

(21) Appl. No.: 16/627,482

(22) PCT Filed: Jul. 31, 2018

(86) PCT No.: PCT/JP2018/028611
§ 371 (c)(1),
(2) Date: Dec. 30, 2019

(87) PCT Pub. No.: WO2019/026891
PCT Pub. Date: Feb. 7, 2019

(65) Prior Publication Data
US 2020/0157326 A1 May 21, 2020

(30) Foreign Application Priority Data

Jul. 31, 2017 (JP) .............................. JP2017-148460
Jan. 31, 2018 (JP) .............................. JP2018-015593

(51) Int. Cl.
*C08L 23/12* (2006.01)
*A61L 15/22* (2006.01)
(Continued)

(52) U.S. Cl.
CPC ............. *C08L 23/12* (2013.01); *A61L 15/225* (2013.01); *A61L 15/585* (2013.01);
(Continued)

(58) Field of Classification Search
CPC .......... C08L 23/12; C08L 23/14; C08L 23/08; C08L 23/22; C08F 297/044; C08F 297/04;
(Continued)

(56) References Cited

U.S. PATENT DOCUMENTS 4,546,150 A 10/1985 Shigemoto
6,657,000 B1 12/2003 De Keyzer et al.
(Continued)

FOREIGN PATENT DOCUMENTS

JP 60-28442 A 2/1985
JP 2003-503553 A 1/2003
(Continued)

OTHER PUBLICATIONS

International Search Report dated Oct. 30, 2018 in PCT/JP2018/028611 filed on Jul. 31, 2018 citing references AK-AS therein, 2 pages.

*Primary Examiner* — Mark S Kaucher
(74) *Attorney, Agent, or Firm* — Oblon, McClelland, Maier & Neustadt, L.L.P.

(57) ABSTRACT

A thermoplastic resin composition containing an olefin-based polymer and a hydrogenated block copolymer, wherein: with respect to the olefin-based polymer, an amount of heat of crystal fusion ($\Delta H$) is less than 80 J/g; the hydrogenated block copolymer is a hydrogenated product of a block copolymer composed of a first polymer block consisting of a structural unit derived from an aromatic vinyl compound and a second polymer block consisting of a structural unit derived from a conjugated diene compound; the content of the first polymer block in the hydrogenated block copolymer is 1 to 60% by mass; a proportion of a vinyl bond amount of the second polymer block is 50 to 95 mol %; and the content of the hydrogenated block copolymer in the thermoplastic resin composition is from 1 to 30 parts by (Continued)

Example 1 mass relative to 100 parts by mass of the total amount of the olefin-based polymer and the hydrogenated block copolymer.

16 Claims, 3 Drawing Sheets

(51) Int. Cl.

| | |
|---|---|
| *A61L 15/58* | (2006.01) |
| *C08F 297/04* | (2006.01) |
| *C08L 23/08* | (2006.01) |
| *C08L 23/14* | (2006.01) |
| *C08L 23/22* | (2006.01) |
| *C09J 123/08* | (2006.01) |
| *C09J 123/12* | (2006.01) |
| *C09J 123/14* | (2006.01) |
| *C09J 123/22* | (2006.01) |

(52) U.S. Cl.
CPC .......... *C08F 297/044* (2013.01); *C08L 23/08* (2013.01); *C08L 23/14* (2013.01); *C08L 23/22* (2013.01); *C09J 123/08* (2013.01); *C09J 123/12* (2013.01); *C09J 123/14* (2013.01); *C09J 123/22* (2013.01); *C08L 2205/05* (2013.01); *C08L 2207/04* (2013.01)

(58) Field of Classification Search
CPC .... C08F 2500/20; C09J 123/12; C09J 123/14; C09J 123/08; C09J 123/22
See application file for complete search history.

(56) References Cited

U.S. PATENT DOCUMENTS

| | | | |
|---|---|---|---|
| 2002/0147274 A1 | 10/2002 | Sasagawa et al. | |
| 2005/0228114 A1* | 10/2005 | Gelles | .................. C09J 153/025 524/502 |
| 2012/0190786 A1 | 7/2012 | Sasaki | |
| 2013/0299731 A1* | 11/2013 | Wright | .................... C08L 25/06 252/62 |
| 2015/0368455 A1* | 12/2015 | Akahori | .................. C08L 53/02 36/25 R |
| 2018/0030195 A1 | 2/2018 | Oshita et al. | |
| 2019/0321242 A1* | 10/2019 | Turner | .................. A61F 13/539 |
| 2019/0338169 A1* | 11/2019 | Matsumura | ............. F21S 43/27 |

FOREIGN PATENT DOCUMENTS

| | | |
|---|---|---|
| JP | 2004-250563 A | 9/2004 |
| JP | 2012-236895 A | 12/2012 |
| JP | 2014-111711 A | 6/2014 |
| JP | 2014-169437 A | 9/2014 |
| JP | 6001685 B2 | 10/2016 |
| JP | 6039693 B2 | 12/2016 |
| WO | WO 01/85818 A1 | 11/2001 |
| WO | WO 2011/040586 A1 | 4/2011 |
| WO | WO 2012/067609 A1 | 5/2012 |
| WO | WO2016/136760 A1 | 9/2016 |

* cited by examiner

Example 1

Comparative Example 2

P: Island of hydrogenated copolymer (b)
Q: Island of olefin-based polymer (a)

THERMOPLASTIC RESIN COMPOSITION, HOT MELT ADHESIVE, AUTOMOBILE MEMBER, AND HYGIENIC MATERIAL MEMBER

TECHNICAL FIELD

The present invention relates to a thermoplastic resin composition, a hot melt adhesive, an automobile member, and a hygienic material member.

BACKGROUND ART

As a base polymer of hot melt adhesives, depending upon an application thereof, ethylene-based copolymers, such as EVA (ethylene-vinyl acetate copolymer), EEA (ethylene-ethyl acrylate copolymer), EAA (ethylene-acrylic acid copolymer), and EMMA (ethylene-methyl methacrylate copolymer), olefin-based resins, such as polyethylene, polypropylene, APAO (amorphous poly-α-olefin), POE (polyolefin elastomer), and an olefin block copolymer (OBC), and synthetic rubbers, such as SIS (styrene-isoprene-styrene copolymer), SBS (styrene-butadiene-styrene copolymer), and hydrogenated products thereof; and besides, polyester resins, polyamide resins, urethane-based resins, and so on are used.

As a pressure-sensitive adhesive using the aforementioned base polymer, for example, non-pressure-sensitive adhesive compositions containing a blend of a poly-α-olefin, a low-viscosity styrene-based block copolymer, and a tackifier resin; pressure-sensitive adhesive compositions containing a specified non-crystalline α-olefin-based copolymer and a specified styrene-based copolymer; and so on are proposed (see PTLs 1 to 3).

In addition, in view of the fact that a hot melt adhesive has such characteristics that when pressure-bonded in a heat-melted state and then cooled, it is solidified to undergo adhesion (hot melt adhesiveness), is free from a solvent so that its safety is high, and it is possible to achieve instantaneous adhesion and high-speed adhesion, the hot melt adhesive is used in a wide range of fields inclusive of paper processing, woodworking, hygienic materials, electronic fields, and the like.

CITATION LIST

Patent Literature

PTL 1: Japanese Patent No. 6001685
PTL 2: JP 2012-236895 A
PTL 3: Japanese Patent No. 6039693

SUMMARY OF INVENTION

Technical Problem

For example, with respect to adhesion of a hygienic material member and adhesion between heterogeneous materials, in which stretchability is demanded, the hot melt adhesive to be used is required to have stretchability.

However, in the pressure-sensitive adhesive compositions described in the aforementioned PTLs 1 to 3, the stretchability was not satisfactory.

In view of such actual circumstances, the present invention has been made and is aimed to provide a thermoplastic resin composition having excellent stretchability and also having high adhesive force and transparency as well as a hot melt adhesive, an automobile member, and a hygienic material member.

Solution to Problem

In order to solve the aforementioned problem, the present inventor made extensive and intensive investigations. As a result, it has been found that the foregoing problem can be solved by the following inventions.

Specifically, the disclosures of the present application are concerned with the following.

[1] A thermoplastic resin composition containing an olefin-based polymer (a) and a hydrogenated block copolymer (b), wherein: with respect to the olefin-based polymer (a), an amount of heat of crystal fusion ($\Delta H$) measured at a heating rate of 10° C./min in differential scanning calorimetry is less than 80 J/g; the hydrogenated block copolymer (b) is a hydrogenated product of a block copolymer composed of a polymer block (A) consisting mainly of a structural unit derived from an aromatic vinyl compound and a polymer block (B) consisting mainly of a structural unit derived from a conjugated diene compound; the content of the polymer block (A) in the hydrogenated block copolymer (b) is from 1 to 60% by mass; a proportion of a vinyl bond amount of the polymer block (B) is from 50 to 95 mol %; the content of the hydrogenated block copolymer (b) in the thermoplastic resin composition is from 1 to 30 parts by mass relative to 100 parts by mass of the total amount of the olefin-based polymer (a) and the hydrogenated block copolymer (b); and the olefin-based polymer (a) and the polymer block (B) of the hydrogenated block copolymer (b) are made miscible with each other on a molecular level.

[2] The thermoplastic resin composition of the above [1], wherein the amount of heat of crystal fusion ($\Delta H$) of the olefin-based polymer (a) is 1 J/g or more and less than 80 J/g.

[3] The thermoplastic resin composition of the above [1] or [2], wherein the olefin-based polymer (a) is at least one olefin-based polymer selected from the group consisting of a non-crystalline or low-crystalline poly-α-olefin and a polyolefin elastomer.

[4] The thermoplastic resin composition of any of the above [1] to [3], wherein the olefin-based polymer (a) is a non-crystalline or low-crystalline poly-α-olefin.

[5] The thermoplastic resin composition of any of the above [1] to [4], wherein a weight average molecular weight of the hydrogenated block copolymer (b) is from 30,000 to 500,000.

[6] The thermoplastic resin composition of any of the above [1] to [5], wherein a molecular weight distribution of the hydrogenated block copolymer (b) is from 1.0 to 1.5.

[7] The thermoplastic resin composition of any of the above [1] to [6], wherein a melt flow rate of the hydrogenated block copolymer (b) measured under a condition at a temperature of 230° C. and a load of 2.16 kg in conformity with JIS K7210-1:2014 is from 0.1 to 90 g/10 min.

[8] The thermoplastic resin composition of any of the above [1] to [7], wherein the content of the polymer block (A) in the hydrogenated block copolymer (b) is from 5 to 9% by mass.

[9] The thermoplastic resin composition of any of the above [1] to [8], wherein the polymer block (B) of the hydrogenated block copolymer (b) is a polymer block consisting mainly of a structural unit derived from a mixture of isoprene and butadiene, and a mixing ratio of isoprene to butadiene [isoprene/butadiene] (molar ratio) is from 10/90 to 90/10.

[10] The thermoplastic resin composition of any of the above [1] to [9], wherein in the temperature dispersion measurement of dynamic viscoelasticity of the thermoplastic resin composition, the number of maximum peaks of a loss modulus (G″) appearing in a temperature range of −70 to 0° C. is one.

[11] The thermoplastic resin composition of any of the above [1] to [10], further containing a tackifier.

[12] A hot melt adhesive containing the thermoplastic resin composition of any of the above [1] to [11].

[13] An automobile member containing the hot melt adhesive of the above [12].

[14] A hygienic material member containing the hot melt adhesive of the above [12].

Advantageous Effects of Invention

In accordance with the present invention, it is possible to provide a thermoplastic resin composition having excellent stretchability and also having high adhesive force and transparency as well as a hot melt adhesive, an automobile member, and a hygienic material member.

DESCRIPTION OF EMBODIMENTS

[Thermoplastic Resin Composition]

The thermoplastic resin composition of the present invention is a thermoplastic resin composition containing an olefin-based polymer (a) and a hydrogenated block copolymer (b), wherein:

with respect to the olefin-based polymer (a), an amount of heat of crystal fusion (ΔH) measured at a heating rate of 10° C./min in differential scanning calorimetry is less than 80 J/g;

the hydrogenated block copolymer (b) is a hydrogenated product of a block copolymer composed of a polymer block (A) consisting mainly of a structural unit derived from an aromatic vinyl compound and a polymer block (B) consisting mainly of a structural unit derived from a conjugated diene compound; the content of the polymer block (A) in the hydrogenated block copolymer (b) is 1 to 60% by mass; a proportion of a vinyl bond amount of the polymer block (B) is 50 to 95 mol %;

the content of the hydrogenated block copolymer (b) in the thermoplastic resin composition is from 1 to 30 parts by mass relative to 100 parts by mass of the total amount of the olefin-based polymer (a) and the hydrogenated block copolymer (b); and the olefin-based polymer (a) and the polymer block (B) of the hydrogenated block copolymer (b) are made miscible with each other on a molecular level.

In the case where the thermoplastic resin composition of the present invention contains the hydrogenated block copolymer (b) in a specified proportion together with the olefin-based polymer (a), the olefin-based polymer (a) and the polymer block (B) of the hydrogenated block copolymer (b) are made miscible with each other on a molecular level. According to this, the thermoplastic resin composition of the present invention has excellent stretchability and also has high adhesive force and transparency.

The fact that the olefin-based polymer (a) and the polymer block (B) of the hydrogenated block copolymer (b) are made miscible with each other on a molecular level can be, for example, confirmed by a method in which a 1 mm-thick sheet obtained by heat pressing a thermoplastic resin composition composed of the olefin-based polymer (a) and the hydrogenated block copolymer (b) is dipped in tetrahydrofuran for 5 minutes to undergo an etching treatment, and then, the sheet surface is observed by a scanning electron microscope (SEM). In the case where the both are made miscible with each other on a molecular level, the surface of the thermoplastic resin composition sheet becomes a uniform surface with less unevenness even after the etching treatment. On the other hand, in the case where the both are not made miscible with each other on a molecular level, the hydrogenated block copolymer (b) is dissolved by the etching treatment and removed, and therefore, a concave having a size of a long side of 10 μm or more is generated on the surface of the thermoplastic resin composition sheet.

Figure 3:
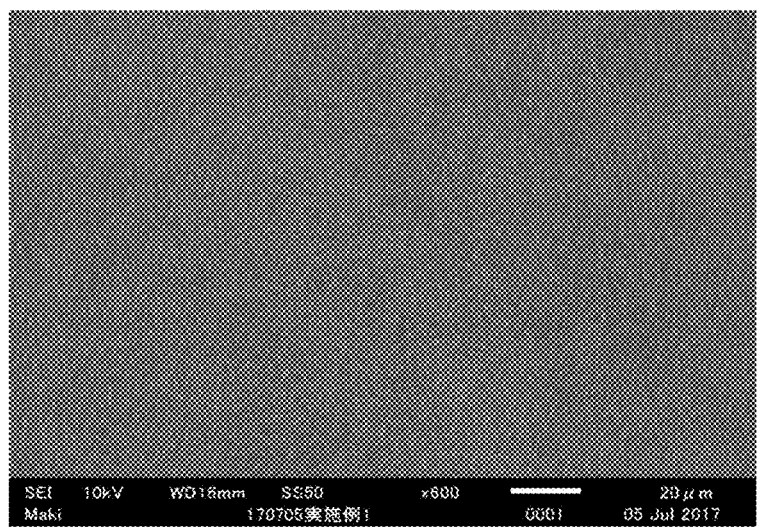
FIG. 3 is an SEM photograph of a surface of a thermoplastic resin composition sheet of Example 1.
Figure 4:
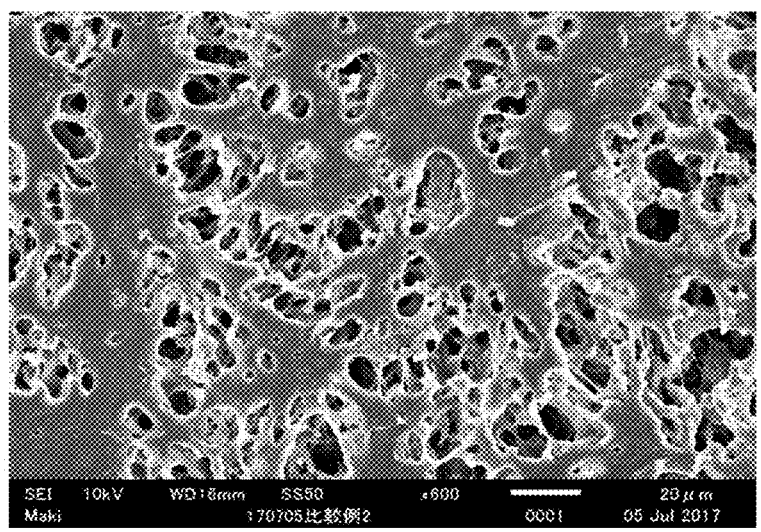
FIG. 4 is an SEM photograph of a surface of a thermoplastic resin composition sheet of Comparative Example 2.

FIG. 3 shows an SEM photograph of a surface of a thermoplastic resin composition sheet of Example 1. As a result of observing a region of 200 μm×150 μm of the surface of the thermoplastic resin composition sheet, it is noted that a concave having a size of a long side of 10 μm or more is not observed, so that the sheet surface is uniform. In addition, FIG. 4 shows an SEM photograph of a surface of a thermoplastic resin composition sheet of Comparative Example 2. As a result of observing a region of 200 μm×150 μm of the surface of the thermoplastic resin composition sheet, a lot of concaves having a size of a long side of 10 μm or more were observed.

In the case where the olefin-based polymer (a) and the polymer block (B) of the hydrogenated block copolymer (b) are made miscible with each other on a molecular level, the size of the long side of the concave is less than 10 μm. In view of the fact that a balance among adhesive force, stretchability, and haze of the thermoplastic resin composition becomes favorable, the size of the long side of the concave is preferably 8 μm or less, more preferably 5 μm or less, and still more preferably 1 μm or less. In addition, though a lower limit value of the size of the long side of the concave is not particularly limited, it may be 0.1 μm or more. Particularly preferred is 0 μm, namely, the state in which the surface of the thermoplastic resin composition sheet is not substantially changed owing to the etching treatment, and in the SEM photograph, the concave is not observed. In this state, the miscibilization on a molecular level is most favorable.

In the case where the thermoplastic resin composition of the present invention is, for example, used as an adhesive, in general, the thermoplastic resin composition is occasionally compounded with a compounding material, such as a tackifier, an oil, and a wax. Even in such a case, in the present invention, the thermoplastic resin composition and the compounding material may be not always made miscible with each other, and so far as the olefin-based polymer (a) and the polymer block (B) of the hydrogenated block copolymer (b) are made miscible with each other on a molecular level, favorable physical properties can be imparted even after being compounded with the compounding material.

For example, in the case where a mixture of the thermoplastic resin composition of the present invention with the compounding material is subjected to SEM observation in the same manner as mentioned above, there is a case where the compounding material which is not made miscible on a molecular level is observed as the concave having a size of a long side of 10 μm or more. However, even in such a case, so far as the olefin-based polymer (a) and the polymer block (B) of the hydrogenated block copolymer (b) are made miscible with each other on a molecular level, favorable physical properties are obtained.

For example, in the case of confirming the fact that the olefin-based polymer (a) and the polymer block (B) of the hydrogenated block copolymer (b) are made miscible with each other on a molecular level, the confirmation can be achieved by subjecting the thermoplastic resin composition composed of only the olefin-based polymer (a) and the hydrogenated block copolymer (b) and not containing a compounding material to SEM observation.

Figure 5:
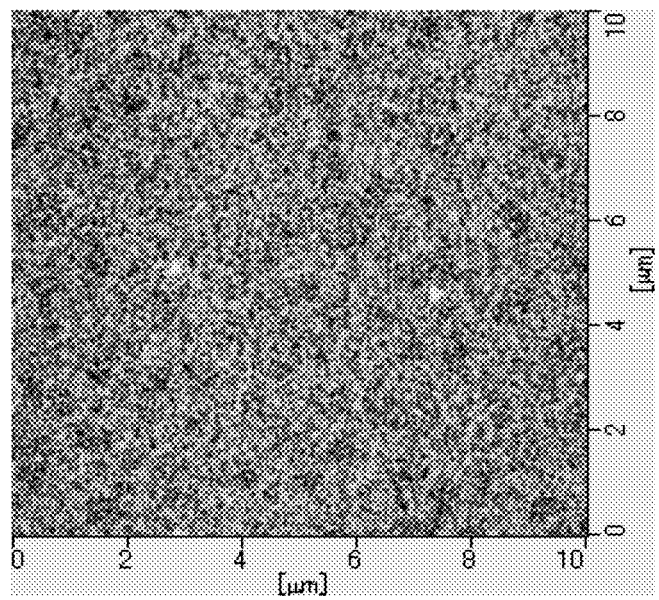
FIG. 5 shows the results of SPM observation of a thermoplastic resin composition sheet of Example 1.
Figure 6:
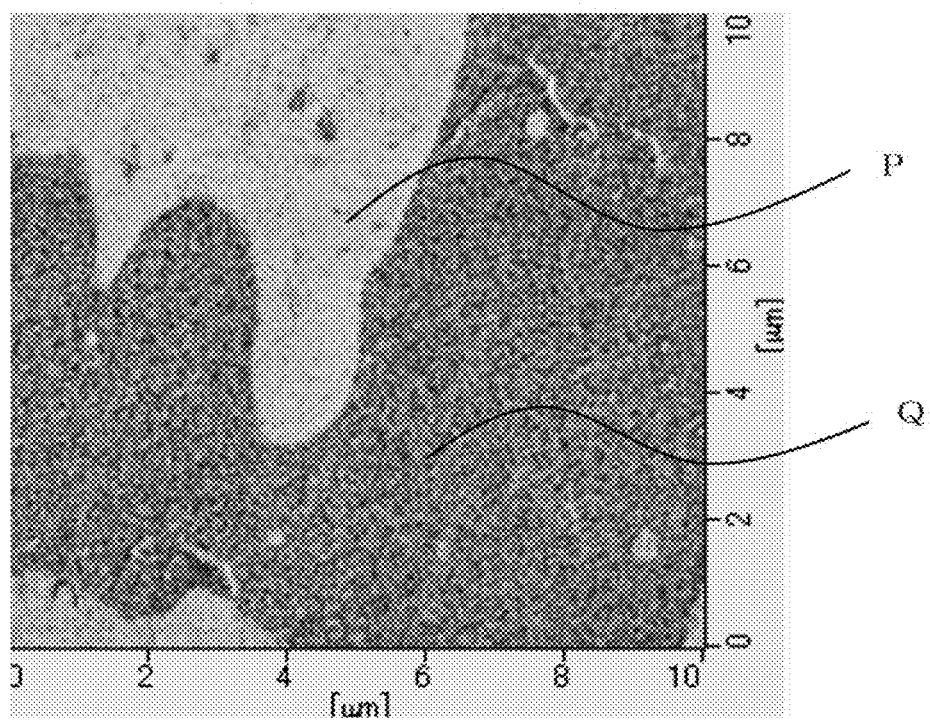
FIG. 6 shows the results of SPM observation of a thermoplastic resin composition sheet of Comparative Example 2.

There is a case where the state that the olefin-based polymer (a) and the polymer block (B) of the hydrogenated block copolymer (b) are made miscible with each other on a molecular level may also be observed by a scanning probe microscope (SPM) on the thermoplastic resin composition composed of the olefin-based polymer (a) and the hydrogenated block copolymer (b). FIG. 5 shows the results of SPM observation of a thermoplastic resin composition sheet of Example 1, and FIG. 6 shows the results of SPM observation of a thermoplastic resin composition sheet of Comparative Example 2. In FIG. 6 in which the both are not made miscible with each other on a molecular level, an island of the olefin-based polymer (a) and an island of the hydrogenated block copolymer (b) are distinguishably observed, whereas in FIG. 5 where the both are made miscible with each other on a molecular level, the entirety is observed in a homogenous state.

When the olefin-based polymer (a) and the polymer block (B) of the hydrogenated block copolymer (b) are made miscible with each other on a molecular level, in the temperature dispersion measurement of dynamic viscoelasticity of the thermoplastic resin composition of the present invention, the number of maximum peaks of a loss modulus (G") appearing in a temperature range of −70 to 0° C. tends to become one. This is caused due to the fact that in the case where the olefin-based polymer (a) and the polymer block (B) of the hydrogenated block copolymer (b) are made miscible with each other on a molecular level, both a maximum peak position of a loss modulus (G"a) of the olefin-based polymer (a) and a maximum peak position of a loss modulus (G"b) derived from the polymer block (B) of the hydrogenated block copolymer (b), as measured in a temperature range of −70 to 0° C. by the temperature dispersion measurement of dynamic viscoelasticity, are shifted, respectively to overlap each other.

Examples of a method for making the olefin-based polymer (a) and the polymer block (B) of the hydrogenated block copolymer (b) miscible with each other on a molecular level include regulation of kind and use amount of each of the olefin-based polymer (a) and the hydrogenated block copolymer (b), regulation of a proportion of a vinyl bond amount of the polymer block (B), and regulation of a viscosity of the olefin-based polymer (a) and a viscosity of the hydrogenated block copolymer (b). Above all, the regulation of a proportion of a vinyl bond amount is especially effective for achieving the miscibilization on a molecular level.

In particular, in the case where the polymer block (B) is a polymer block consisting mainly of a structural unit derived from a mixture of isoprene and butadiene, a mixing ratio of isoprene to butadiene [isoprene/butadiene] (molar ratio) is 10/90 to 90/10, a proportion of the vinyl bond amount of the polymer block (B) is 50 to 95 mol %, and a hydrogenation rate of the polymer block (B) is 85 mol % or more, the miscibility between the olefin-based polymer (a) and the polymer block (B) is especially enhanced, so that the olefin-based polymer (a) and the polymer block (B) of the hydrogenated block copolymer (b) can be more easily made miscible with each other on a molecular level.

The mixing ratio of isoprene to butadiene [isoprene/butadiene] (molar ratio) and the proportion of the vinyl bond amount of the polymer block (B) can be adjusted while defining a solubility parameter (SP value) of the polymer block (B) as an index. From the viewpoint that the miscibility between the olefin-based polymer (a) and the polymer block (B) is enhanced, the SP value of the polymer block (B) is preferably 17.25 $MPa^{1/2}$ or less, more preferably 17.15 $MPa^{1/2}$ or less, still more preferably 17.13 $MPa^{1/2}$ or less, and especially preferably 17.11 $MPa^{1/2}$ or less. In addition, the SP value of the polymer block (B) may be 16.00 $MPa^{1/2}$ or more, may be 16.40 $MPa^{1/2}$ or more, may be 16.85 $MPa^{1/2}$ or more, and may be 17.00 $MPa^{1/2}$ or more.

The SP value can be calculated by the Hoy method on a basis of a structure of polymer. In detail, the Hoy method is described in "Properties of Polymers (4th Edition): D. W. van Krevelen, Klaas to Nijenhuis; Elsevier Science, 2009". In addition, in the case where the SP value cannot be calculated by the Hoy method, then, the solubility parameter can be calculated by an experimental method by judgement on whether or not the polymer is dissolved in a known solvent. In detail, the aforementioned experimental method is described in "Polymer handbook (4th Edition): J. Brandrup, E. H. Immergut, E. A. Grulke (Eds.); Wiley, New York, 1999".

[Olefin-based Polymer (a)]

In the olefin-based polymer (a) which is used in the present invention, an amount of heat of crystal fusion (ΔH) measured at a heating rate of 10° C./min in differential scanning calorimetry is less than 80 J/g. When the αH is 80 J/g or more, the stretchability of the thermoplastic resin composition disappears, and on the occasion of using the thermoplastic resin composition as a hot melt adhesive, the adhesive force becomes low. From the viewpoint of stretchability, heat resistance, and so on, the ΔH of the olefin-based polymer (a) may be appropriately set within the range of less than 80 J/g, and for example, from the viewpoint of enhancing the stretchability, the ΔH is preferably 1 J/g or more and less than 80 J/g, more preferably 2 to 40 J/g, and still more preferably 5 to 25 J/g. In addition, from the viewpoint of heat resistance, the ΔH is preferably 5 to 70 J/g, more preferably 10 to 60 J/g, and still more preferably 15 to 50 J/g.

The amount of heat of crystal fusion (ΔH) is one obtained on the occasion of subjecting a sample to temperature rise by a differential scanning calorimeter (DSC) at a heating rate of 10° C./min from 30° C. to 180° C. (heating step 1) to fuse it; and then cooling the sample from 180° C. to −70° C. to achieve crystallization (cooling step); further undergoing temperature rise at a heating rate of 10° C./min from −70° C. to 180° C. (heating step 2), analyzing an endothermic peak appearing in the heating step 2.

Although the olefin-based polymer (a) is not particularly limited so far as the amount of heat of crystal fusion (ΔH) is less than 80 J/g, from the viewpoint that on the occasion of using the thermoplastic resin composition as a hot melt adhesive, the adhesive force becomes high, it is preferably at least one olefin-based polymer selected from a non-crystalline or low-crystalline poly-α-olefin (amorphous poly-α-olefin) and a polyolefin elastomer, and more preferably a non-crystalline or low-crystalline poly-α-olefin.

Examples of the non-crystalline or low-crystalline poly-α-olefin include a propylene homopolymer, an ethylene-propylene copolymer, a propylene-1-butene random copolymer, and a propylene-ethylene-1-butene random copolymer. Above all, from the viewpoint of transparency, a propylene homopolymer and an ethylene-propylene copolymer are preferred.

Examples of commercially available products of the non-crystalline or low-crystalline poly-α-olefin (APAO, amorphous poly-α-olefin) include REXtac RT2115, RT2180, RT2215, RT2280, RT2304, RT2315, RT2535, RT2585, RT2730, RT2780, RT2788, RT6825, E101, and RT9720, all of which are manufactured by REXtac LLC; Vestoplast 508, 703, 704, 708, 750, 751, 792, 828, 888, and EP X55, all of which are manufactured by Evonik Industries AG; and Eastoflex E1016PL-1, P1010, P1023, E1060, E1200, D-178, and M1058, all of which are manufactured by Eastman Chemical Company.

Examples of the polyolefin elastomer (POE) include a polyethylene-based elastomer and a polypropylene-based elastomer. The polyethylene-based elastomer as referred to herein means an elastomer containing 50% by mass or more of ethylene, and the polypropylene-based elastomer as referred to herein means an elastomer containing 50% by mass or more of propylene. Above all, a polyethylene-based elastomer is preferably used. When the polyethylene-based elastomer is used, its low-temperature characteristics are excellent. Meanwhile, in the case where the heat resistance is required, a polypropylene-based elastomer is preferably used. In addition, a modified polyolefin elastomer obtained through copolymerization with a copolymerizable monomer, such as an α-olefin, vinyl acetate, and an alkyl (meth) acrylate, can be used.

Examples of commercially available products of the polyolefin elastomer (POE) include ENGAGE 8000 Series and 7000 Series, all of which are manufactured by Dow Chemical Company; AFFINITY GA 1900, 1950, 1875, and 1000R, all of which are manufactured by Dow Chemical Company; Vistamaxx 8380, 8780, 8880, 6102, 6202, 6502, 3000, 3020, 3588FL, and 3980FL, all of which are manufactured by Exxon Mobil Corporation; and TAFMER DF Series, A Series, P Series, and XM Series, all of which are manufactured by Mitsui Chemicals, Inc.

The content of the olefin-based polymer (a) is preferably 5 to 99 parts by mass, more preferably 10 to 90 parts by mass, still more preferably 20 to 80 parts by mass, and yet still more preferably 25 to 75 parts by mass relative to the whole amount of the thermoplastic resin composition.

The content of the olefin-based polymer (a) is preferably 70 to 99 parts by mass, more preferably 75 to 98 parts by mass, still more preferably 75 to 95 parts by mass, yet still more preferably 78 to 95 parts by mass, and especially preferably 80 to 95 parts by mass relative to 100 parts by mass of the total amount of the olefin-based polymer (a) and the hydrogenated block copolymer (b). So far as the content of the olefin-based polymer (a) falls within the aforementioned range, on the occasion of using the thermoplastic resin composition as a hot melt adhesive, it is excellent in hot melt coating properties.

[Hydrogenated Block Copolymer (b)]

The hydrogenated block copolymer (b) which is used in the present invention is a hydrogenated product composed of a polymer block (A) consisting mainly of a structural unit derived from an aromatic vinyl compound and a polymer block (B) consisting mainly of a structural unit derived from a conjugated diene compound.

(Polymer Block (A))

The polymer block (A) is one consisting mainly of a structural unit derived from an aromatic vinyl compound (hereinafter occasionally abbreviated as "aromatic vinyl compound unit"). The wording "consisting mainly of" as referred to herein refers to the fact that the aromatic vinyl compound unit is contained in an amount of more than 50% by mass based on the total mass of the polymer block (A). From the viewpoint that the stretchability of the thermoplastic resin composition is enhanced and that the haze is reduced to reveal excellent transparency, the content of the aromatic vinyl compound unit in the polymer block (A) is preferably 70% by mass or more, more preferably 80% by mass or more, still more preferably 90% by mass or more, and yet still more preferably 95% by mass or more based on the total mass of the polymer block (A), and it may also be substantially 100% by mass.

Examples of the aromatic vinyl compound include styrene, o-methylstyrene, m-methylstyrene, p-methylstyrene, α-methylstyrene, β-methylstyrene, 2,6-dimethylstyrene, 2,4-dimethylstyrene, α-methyl-o-methylstyrene, α-methyl-m-methylstyrene, α-methyl-p-methylstyrene, β-methyl-o-methylstyrene, β-methyl-m-methylstyrene, β-methyl-p-methylstyrene, 2,4,6-trimethylstyrene, α-methyl-2,6-dimethylstyrene, α-methyl-2,4-dimethylstyrene, β-methyl-2,6-dimethylstyrene, β-methyl-2,4-dimethylstyrene, o-chlorostyrene, m-chlorostyrene, p-chlorostyrene, 2,6-dichlorostyrene, 2,4-dichlorostyrene, α-chloro-o-chlorostyrene, α-chloro-m-chlorostyrene, α-chloro-p-chlorostyrene, β-chloro-o-chlorostyrene, β-chloro-m-chlorostyrene, β-chloro-p-chlorostyrene, 2,4,6-trichlorostyrene, α-chloro-2,6-dichlorostyrene, α-chloro-2,4-dichlorostyrene, β3-chloro-2,6-dichlorostyrene, β-chloro-2,4-dichlorostyrene, o-t-butylstyrene, m-t-butylstyrene, p-t-butylstyrene, o-methoxystyrene, m-methoxystyrene, p-methoxystyrene, o-chloromethylstyrene, m-chloromethylstyrene, p-chloromethylstyrene, o-bromomethylstyrene, m-bromomethylstyrene, p-bromomethylstyrene, a silyl group-substituted styrene derivative, indene, and vinylnaphthalene. These aromatic vinyl compounds may be used alone or may be used in combination of two or more thereof.

Above all, from the viewpoint of a balance of production cost and physical properties, styrene, α-methylstyrene, p-methylstyrene, and a mixture thereof are preferred, and styrene is more preferred.

However, so far as not interfering with the objects and the effects of the present invention, the polymer block (A) may contain a structural unit derived from any other unsaturated monomer than aromatic vinyl compounds (hereinafter occasionally abbreviated as "other unsaturated monomer unit") in a proportion of 50% by mass or less. Examples of the other unsaturated monomer include at least one selected from the group consisting of conjugated diene compounds, such as isoprene, butadiene, 1,3-hexadiene, 2,3-dimethyl-1, 3-butadiene, 1,3-pentadiene, myrcene, 1,3-cyclopentadiene, 1, 3-cyclohexadiene, 1,3-cyclopentadiene, and 1,3-cyclooctadiene; methacrylic acid esters, such as methyl methacrylate, ethyl methacrylate, and butyl methacrylate; acrylic acid esters, such as methyl acrylate, ethyl acrylate, and butyl acrylate; methyl vinyl ether, N-vinylcarbazole, isobutylene, β-pinene, menthene, dipentene, methylene norbornene, and 2-methylenetetrahydrofuran. The bonding mode in the case where the polymer block (A) contains the foregoing other unsaturated monomer unit is not particularly limited, and it may be any of random, tapered, and completely alternate ones.

The content of the structural unit derived from the other unsaturated monomer unit in the polymer block (A) is preferably 30% by mass or less, more preferably 10% by mass or less, still more preferably 5% by mass or less, and yet still more preferably 0% by mass.

The block copolymer may have at least one polymer block (A). In the case where the block copolymer has two or more of the polymer blocks (A), those polymer blocks (A) may be the same as or may be different from each other. In this specification, the wording "the polymer blocks are different" means that at least one of the monomer units constituting the polymer block, the weight average molecular weight, and the stereoregularity, and in the case where the block has plural monomer units, the ratio of the respective monomer units and the copolymerization mode (random, tapered, or completely alternate) is different.

Although a weight average molecular weight (Mw) of the polymer block (A) which the block copolymer has is not particularly limited, among the polymer blocks (A) which the block copolymer has, the weight average molecular weight of at least one polymer block (A) is preferably 2,000 to 60,000, and more preferably 4,000 to 50,000. When the block copolymer has at least one polymer block (A) having a weight average molecular weight falling within the aforementioned range, the stretchability of the thermoplastic resin composition is revealed.

The "weight average molecular weight" described in this specification and the claims is everywhere a weight average molecular weight expressed in terms of standard polystyrene as determined by the gel permeation chromatography (GPC). The weight average molecular weight of each of the polymer blocks (A) which the block copolymer has can be determined by measuring the liquid that is sampled every time after completion of the polymerization of each polymer block in the production process. In addition, for example, in the case of a triblock copolymer having an A1-B-A2 structure obtained by block copolymerization of A1, B, and A2 in sequence, the weight average molecular weight of the first polymer block A1 can be determined by subjecting the liquid that is sampled on the occasion of completion of the polymerization of the polymer block A1 to the GPC measurement. In addition, the weight average molecular weight of the polymer block B can be determined by subjecting the liquid that is sampled after on the occasion of completion of the polymerization of the polymer block B to the GPC measurement to determine the weight average molecular weight of a diblock copolymer having an A1-B structure, from which value is then subtracted the weight average molecular weight of the polymer block A1 determined according to the aforementioned method. Furthermore, the weight average molecular weight of the polymer block A2 can be determined by subjecting the liquid that is sampled after on the occasion of completion of the polymerization of the polymer block A2 to the GPC measurement to determine the weight average molecular weight of a triblock copolymer having an A1-B-A2 structure, from which value is then subtracted the weight average molecular weight of the diblock copolymer having an A1-B structure determined according to the aforementioned method. In addition, as another method, in the case of the triblock copolymer having an A1-B-A2 structure, the total weight average molecular weight of the polymer block (A) is calculated from the weight average molecular weight of the triblock copolymer and the total content of the polymer block (A) in the triblock copolymer to be confirmed through the $^1$H-NMR measurement, subsequently, the weight average molecular weight of the polymer block A1 to be confirmed as a deactivated component of a minute amount in the GPC measurement of the triblock copolymer is calculated, and the calculated value is subtracted from the total weight average molecular weight of the polymer block (A) determined according to the aforementioned method, whereby the weight average molecular weight of the polymer block A2 can also be determined.

In the aforementioned block copolymer, the content of the polymer block (A) (in the case where the copolymer has plural polymer blocks (A), the total content thereof) is 1 to 60% by mass. When the content of the polymer block (A) is less than 1% by mass, a cohesive force of the thermoplastic resin composition would be lowered, restoration properties after being deformed would be lowered, and on the occasion of using the thermoplastic resin composition as a hot melt adhesive, an adhesive force would be lowered. On the other hand, when the content of the polymer block (A) is more than 60% by mass, the stretchability of the thermoplastic resin composition is lowered, and on the occasion of using the thermoplastic resin composition as a hot melt adhesive, adhesive properties to an adherend are occasionally lowered. From the same viewpoint, the content of the polymer block (A) is preferably 2 to 40% by mass, more preferably 3 to 20% by mass, still more preferably 4 to 15% by mass, yet still more preferably 5 to 9% by mass, and especially preferably 6 to 9% by mass. In addition, from the viewpoint of improving the transparency of the thermoplastic resin composition, the content of the polymer block (A) is preferably 3 to 15% by mass, more preferably 3 to 9% by mass, and still more preferably 3 to 5% by mass.

The content of the polymer block (A) in the block copolymer is a value determined by the $^1$H-NMR measurement, and in more detail, it is a value measured according to the method described in the section of Examples.

(Polymer Block (B))

The polymer block (B) is one consisting mainly of a structural unit derived from a conjugated diene compound (hereinafter occasionally abbreviated as "conjugated diene compound unit"). The wording "consisting mainly of" as referred to herein refers to the fact that the conjugated diene compound unit is contained in an amount of more than 50% by mass based on the total mass of the polymer block (B). From the viewpoint that the miscibility of the olefin-based polymer (a) that is a component of the thermoplastic resin composition with the polymer block (B) is enhanced and that on the occasion of using the thermoplastic resin composition as a hot melt adhesive, the stretchability and the adhesive force are improved, the content of the conjugated diene compound unit in the polymer block (B) is preferably 70% by mass or more, more preferably 80% by mass or more, still more preferably 90% by mass or more, and yet still more preferably 95% by mass or more based on the total mass of the polymer block (B), and it may also be substantially 100% by mass.

Examples of the conjugated diene compound include isoprene, butadiene, 1,3-hexadiene, 2,3-dimethyl-1,3-butadiene, 1,3-pentadiene, myrcene, 1,3-cyclopentadiene, 1,3-cyclohexadiene, 1,3-cycloheptadiene, and 1,3-cyclooctadiene. Above all, from the viewpoint of making the olefin-based polymer (a) and the polymer block (B) of the hydrogenated block copolymer (b) miscible with each other on a molecular level and improving the stretchability, isoprene, butadiene, and a mixture of isoprene and butadiene are preferred, and isoprene and a mixture of isoprene and butadiene are more preferred. In addition, from the viewpoint of improving the transparency, a mixture of isoprene and butadiene is preferred. In the case of a mixture of isoprene and butadiene, though a mixing ratio thereof [isoprene/butadiene] (molar ratio) is not particularly limited, it is preferably 10/90 to 90/10, more preferably 30/70 to 80/20, still more preferably 40/60 to 70/30, yet still more preferably 45/55 to 60/40, and especially preferably 45/55 to 50/50.

In the case where the polymer block (B) has two or more structural units, a bonding mode thereof may be any of random, tapered, and completely alternate ones, or a combination of two or more thereof.

In the case where the structural unit constituting the polymer block (B) is any of an isoprene unit, a butadiene unit, and a mixed unit of isoprene and butadiene, with respect to the bonding mode of each of isoprene and butadiene, in the case of butadiene, a 1,2-bond or a 1,4-bond can be taken, and in the case of isoprene, a 1,2-bond, a 3,4-bond, or a 1,4-bond can be taken.

In the block copolymer, a proportion of the total content of the 3,4-bond unit and the 1,2-bond unit (vinyl bond amount) in the polymer block (B) is 50 to 95 mol %. When the proportion of the vinyl bond amount is less than 50 mol %, the miscibility between the olefin-based polymer (a) and the polymer block (B) becomes low, and on the occasion of using the thermoplastic resin composition as a hot melt adhesive, the stretchability and the adhesive force cannot be enhanced. This is estimated to be caused due to the fact that in the case where the proportion of the vinyl bond amount is 50 mol % or more, the polymer block (B) and the olefin-based polymer (a) become close in terms of an SP value (solubility parameter), thereby contributing to the miscibility. In addition, when the proportion of the vinyl bond amount is more than 95 mol %, a glass transition temperature of the polymer block (B) becomes high, and flexibility at room temperature is lowered. From such a viewpoint, the proportion of the vinyl bond amount is preferably 55 to 90 mol %, more preferably 56 to 80 mol %, and still more preferably 58 to 70 mol %.

Here, the proportion of the vinyl bond amount is a value calculated by the $^1$H-NMR measurement according to the method described in the section of Examples.

In the case where the polymer block (B) is composed of only butadiene, the aforementioned phrase "content of the 3,4-bond unit and the 1,2-bond unit" is deemed to be replaced with "content of the 1,2-bond unit".

In the block copolymer, the content of the polymer block (B) (in the case where the copolymer has plural polymer blocks (B), the total content thereof) is preferably 40 to 99% by mass. When the content of the polymer block (B) is more than 99 mol %, a cohesive force of the thermoplastic resin composition would be lowered, restoration properties after being deformed would be lowered, and on the occasion of using the thermoplastic resin composition as a hot melt adhesive, an adhesive force would be lowered. On the other hand, when the content of the polymer block (B) is less than 40% by mass, the stretchability of the resin composition is lowered, and on the occasion of using the thermoplastic resin composition as a hot melt adhesive, adhesive properties to an adherend are occasionally lowered. From the same viewpoint, the content of the polymer block (B) is preferably 60 to 98% by mass, more preferably 80 to 97% by mass, still more preferably 85 to 96% by mass, yet still more preferably 91 to 95% by mass, and especially preferably 91 to 94% by mass. In addition, from the viewpoint of improving the transparency of the thermoplastic resin composition, the content of the polymer block (B) is preferably 85 to 97% by mass, more preferably 91 to 97% by mass, and still more preferably 95 to 97% by mass.

The content of the polymer block (B) in the block copolymer is a value determined by the $^1$H-NMR measurement, and in more detail, it is a value measured according to the method described in the section of Examples.

So far as not interfering with the objects and the effects of the present invention, the polymer block (B) may contain a structural unit derived from any other polymerizable monomer than conjugated diene compounds. In this case, in the polymer block (B), the content of the structural unit derived from any other polymerizable monomer than conjugated diene compounds is preferably 50% by mass or less, more preferably 40% by mass or less, still more preferably 30% by mass or less, and yet still more preferably 20% by mass or less. Although a lower limit value of the content of the structural unit derived from any other polymerizable monomer than conjugated diene compounds is not particularly limited, it may be 0% by mass, may be 5% by mass, and may be 10% by mass.

Preferably, examples of the other polymerizable monomer include at least one compound selected from the group consisting of aromatic vinyl compounds, such as styrene, α-methylstyrene, o-methylstyrene, m-methylstyrene, p-methylstyrene, p-t-butylstyrene, 2,4-dimethylstyrene, vinylnaphthalene, and vinylanthracene; methacrylic acid esters, such as methyl methacrylate, ethyl methacrylate, and butyl methacrylate; acrylic acid esters, such as methyl acrylate, ethyl acrylate, and butyl acrylate; methyl vinyl ether, N-vinylcarbazole, isobutylene, β-pinene, menthene, dipentene, methylene norbornene, and 2-methylenetetrahydrofurane. Above all, styrene, α-methylstyrene, and p-methylstyrene are preferred, and styrene is more preferred.

In the case where the polymer block (B) contains a structural unit derived from other polymerizable monomer than conjugated diene compounds, as a specific combination thereof, a combination of isoprene and styrene, a combination of butadiene and styrene, and a combination of isoprene, butadiene, and styrene are preferred; a combination of isoprene and styrene and a combination of isoprene, butadiene, and styrene are more preferred; a combination of isoprene and styrene is still more preferred.

In the case where the polymer block (B) contains a structural unit derived from other polymerizable monomer than conjugated diene compounds, though a bonding mode thereof is not particularly limited and may be any of random, tapered, and completely alternate ones, it is preferably a random one.

The block copolymer may contain at least one aforementioned polymer block (B). In the case where the block copolymer has two or more polymer blocks (B), these polymer blocks (B) may be the same as or different from each other.

(Bonding Mode of Polymer Block (A) and Polymer Block (B))

In the block copolymer, so far as the polymer block (A) and the polymer block (B) bond to each other, a bonding mode thereof is not limited, and it may be any of linear, branched, and radial bonding modes, or a combination of two or more of these bonding modes. Above all, the bonding mode of the polymer block (A) and the polymer block (B)

is preferably a linear bonding mode. When the polymer block (A) is represented by A, and the polymer block (B) is represented by B, examples of the bonding mode include a diblock copolymer represented by A-B; a triblock copolymer represented by A-B-A or B-A-B; a tetrablock copolymer represented by A-B-A-B, A-B-B-A, B-A-A-B, or A-A-B-B; a pentablock copolymer represented by A-B-A-B-A or B-A-B-A-B; and an $(A-B)_nX$-type copolymer (wherein X represents a coupling agent residue, and n represents an integer of 3 or more). Above all, a linear triblock copolymer or a diblock copolymer is preferred, and an A-B-A-type triblock copolymer is preferably used from the viewpoint of flexibility, easiness of production, and so on.

Here, in this specification, in the case where polymer blocks of the same kind linearly bond to each other via a bifunctional coupling agent or the like, the whole of the polymer blocks bonded are dealt as one polymer block. According to this, including the aforementioned exemplifications, the polymer block to be technically strictly expressed as Y-X-Y (wherein X represents a coupling residue) is expressed as Y as a whole, except for the case where it must be specifically differentiated from a single polymer block Y. In this specification, the polymer block of this kind that contains a coupling agent residue is dealt in the manner as mentioned above, and therefore, for example, a block copolymer that contains a coupling agent residue and is to be strictly expressed as A-B-X-B-A (wherein X represents a coupling agent residue) is expressed as A-B-A and is dealt as an example of a triblock copolymer.

The hydrogenated block copolymer (b) is a hydrogenated product of the aforementioned block copolymer.

From the viewpoint that the miscibility between the olefin-based polymer (a) and the polymer block (B) of the hydrogenated block copolymer (b) is enhanced, a carbon-carbon double bond which the polymer block (B) has is hydrogenated in a ratio of preferably 50 mol % or more, more preferably 70 mol % or more, still more preferably 80 mol % or more, yet still more preferably 85 mol % or more, and especially preferably 90 mol % or more. The foregoing value is also referred to as "hydrogenation rate". Although an upper limit value of the hydrogenation rate is not particularly limited, the upper limit value may be 99 mol % and may be 98 mol %.

The hydrogenation rate is a value determined after the hydrogenation through the $^1$-NMR measurement from the content of the carbon-carbon double bond in the structural unit derived from the conjugated diene compound in the polymer block (B), and in more detail, it is a value measure according to the method described in the section of Examples.

A weight average molecular weight (Mw) of the hydrogenated block copolymer (b), which is expressed in terms of standard polystyrene according to the gel permeation chromatography (GPC), is preferably 30,000 to 500,000, more preferably 50,000 to 400,000, still more preferably 80,000 to 300,000, yet still more preferably 100,000 to 200,000, and especially preferably 150,000 to 200,000. When the weight average molecular weight of the hydrogenated block copolymer (b) is 30,000 or more, the stretchability of the thermoplastic resin composition becomes high. When the weight average molecular weight of the hydrogenated block copolymer (b) is 500,000 or less, the miscibility between the olefin-based polymer (a) and the polymer block (B) of the hydrogenated block copolymer (b) becomes high, and on the occasion of using the thermoplastic resin composition as a hot melt adhesive, it is excellent in hot melt coating properties.

From the viewpoint that on the occasion of using the thermoplastic resin composition as a hot melt adhesive, the heat resistance becomes high, and bleed-out into an adherend becomes is reduced, the molecular weight distribution (Mw/Mn) of the hydrogenated block copolymer (b) is preferably 1.0 to 1.5, more preferably 1.0 to 1.3, still more preferably 1.0 to 1.2, especially preferably 1.0 to 1.1, and most preferably 1.0 to 1.05.

In the present invention, the molecular weight distribution (Mw/Mn) is a value calculated from the weight average molecular weight Mw and the number average molecular weight Mn expressed in terms of standard polystyrene as measured by the gel permeation chromatography (GPC) method.

From the viewpoint that the miscibility between the olefin-based polymer (a) and the polymer block (B) of the hydrogenated block copolymer (b) becomes high, and that on the occasion of using the thermoplastic resin composition as a hot melt adhesive, it is excellent in hot melt coating properties, a melt flow rate (MFR) of the hydrogenated block copolymer (b), which is measured under a condition at a temperature of 230° C. and a load of 2.16 kg in conformity with JIS K7210-1:2014, is preferably 0.1 to 90 g/10 min, more preferably 1 to 80 g/10 min, still more preferably 2 to 60 g/10 min, yet still more preferably 5 to 40 g/10 min, and especially preferably 10 to 30 g/10 min.

(Production Method of Hydrogenated Block Copolymer (b))

The hydrogenated block copolymer (b) can be produced according to a solution polymerization method, an emulsion polymerization method, a solid-phase polymerization method, or the like. Above all, a solution polymerization method is preferred, and for example, a known method, such as an ionic polymerization method, e.g., anionic polymerization and cationic polymerization, and a radical polymerization method, is applicable. Above all, an anionic polymerization method is preferred. In an anionic polymerization method, an aromatic vinyl compound and a conjugated diene compound are added in the presence of a solvent, an anionic polymerization initiator, and optionally a Lewis base, to give a block copolymer, and if desired, a coupling agent is added to allow the contents to react with each other, followed by hydrogenating the block copolymer, thereby enabling the hydrogenated block copolymer (b) to be obtained.

The content of the hydrogenated block copolymer (b) which is contained in the thermoplastic resin composition of the present invention is 1 to 30 parts by mass relative to 100 parts by mass of the total amount of the olefin-based polymer (a) and the hydrogenated block copolymer (b). When the content of the hydrogenated block copolymer (b) is less than 1 part by mass, the stretchability cannot be enhanced, whereas when it is more than 30 parts by mass, on the occasion of using the thermoplastic resin composition as a hot melt adhesive, the adhesive force is lowered. From such a viewpoint, the content of the hydrogenated block copolymer (b) is preferably 2 to 25 parts by mass, more preferably 5 to 25 parts by mass, still more preferably 5 to 22 parts by mass, and especially preferably 5 to 20 parts by mass.

From the viewpoint of enhancing the adhesive force, it is preferred that the thermoplastic resin composition of the present invention further contains a tackifier.

Examples of the tackifier include coumarone resins, such as a coumarone-indene resin; phenol-based resins and terpene-based resins, such as p-t-butylphenol-acetylene resin, a phenol-formaldehyde resin, a terpene-phenol resin, a polyterpene resin, and a xylene-formaldehyde resin; petroleum resins, such as an aromatic petroleum resin, an aliphatic petroleum resin, an alicyclic petroleum resin, and a modified alicyclic petroleum resin; and rosin-based resins, such as a rosin ester represented by a rosin pentaerythritol ester and a rosin glycerol ester, a hydrogenated rosin, a hydrogenated rosin methyl ester, a polymerized rosin pentaerythritol ester, a hydrogenated rosin ester, a high-melting point ester-based resin, a polymerized rosin, a hardened rosin, and a special rosin ester. Above all, terpene-based resins, petroleum resins, and rosin-based resins are preferred, and petroleum resins are more preferred. The tackifier may be used alone or may be used in combination of two or more thereof.

A softening point of the tackifier is preferably 70 to 160° C., more preferably 80 to 140° C., and still more preferably 85 to 120° C. When the softening point of the tackifier is 70° C. or higher, on the occasion of using the thermoplastic resin composition as a hot melt adhesive, the heat resistance becomes high, and bleed-out into an adherend tends to be reduced, whereas when it is 160° C. or lower, the hot melt coating properties and the processability tend to become favorable.

In the case where the thermoplastic resin composition of the present invention contains the tackifier, its compounding amount is preferably 1 to 50 parts by mass, more preferably 5 to 40 parts by mass, and still more preferably 10 to 30 parts by mass relative to the whole amount of the thermoplastic resin composition.

Within a range where the effects of the present invention are not impaired, if desired, the thermoplastic resin composition of the present invention may further contain an arbitrary component, for example, various additives, such as a plasticizer, e.g., a paraffin-based oil, a wax, a colorant, a flame retardant, a UV absorbent, an antioxidant, a hydrolysis resistance-improving agent, an antifungal agent, an antimicrobial agent, and a stabilizer; various fibers, such as a glass fiber and a polyester fiber; and fillers, such as talc, silica, and a wood meal.

The thermoplastic resin composition of the present invention is not particularly limited with respect to a preparation method thereof, and it can be prepared utilizing a known means. For example, the thermoplastic resin composition of the present invention can be prepared by mixing the olefin-based polymer (a) and the hydrogenated block copolymer (b) and optionally other component using a mixing machine, such as a Henschel mixer, a V blender, a ribbon blender, a tumbler blender, and a conical blender; or thereafter, further undergoing melt kneading or melt mixing at 80 to 250° C. using a kneading machine, such as a single-screw extruder, a twin-screw extruder, a kneader, a Banbury mixer, a roll, and an agitation-type mixing apparatus. In addition, the thermoplastic resin composition can also be prepared by dissolving the respective components [at least the olefin-based polymer (a) and the hydrogenated block copolymer (b)] in a solvent in which the respective components are soluble and mixing, followed by removing the solvent.

(Physical Properties of Thermoplastic Resin Composition)

In general, for example, the hot melt adhesive is used by compounding the thermoplastic resin composition with a compounding material, such as a tackifier, an oil, and a wax, depending upon the purpose of a user, to appropriately adjust the physical properties. So far as the thermoplastic resin composition of the present invention is concerned, even when it is compounded with the compounding material, favorable physical properties which the thermoplastic resin composition has are reflected, and the physical properties after being compounded with the compounding material also become favorable.

A glass transition temperature (Tg) of the thermoplastic resin composition of the present invention is preferably −15 to −50° C., and more preferably −20 to −40° C. When the glass transition temperature (Tg) falls within the aforementioned range, not only the stretchability at a low temperature is high, but also in the case of using the thermoplastic resin composition as a hot melt adhesive, the adhesive force becomes high.

The glass transition temperature (Tg) can be measured by the method described in the section of Examples.

From the viewpoint of transparency, a haze of the thermoplastic resin composition of the present invention is preferably 80% or less, more preferably 60% or less, still more preferably 30% or less, yet still more preferably 27% or less, and especially preferably 25% or less. The haze can be measured by the method in conformity with JIS K7136: 2000.

In the thermoplastic resin composition of the present invention, the adhesive force resulting from the measurement of a peel strength by a T-type peeling test in conformity with JIS L1086:2013 is preferably 25 N/25 mm or more, more preferably 30 N/25 mm or more, and still more preferably 40 N/25 mm or more.

[Hot Melt Adhesive]

The hot melt adhesive of the present invention contains the aforementioned thermoplastic resin composition. According to this, the hot melt adhesive has excellent stretchability and also has high adhesive force and transparency.

The hot melt adhesive of the present invention can be used for various applications. For example, the hot melt adhesive of the present invention can be suitably used for adhesive or sealing applications of automobile members inclusive of a coated exterior panel, a wheel, a mirror, a window, a light, a light cover, a film for interior decoration, a film for exterior decoration, a door garnish molding, a ceiling, a dashboard, an instrument panel, a sheet, a rear tray, a seating seat, an interior skin member, a floor mat, a trunk floor, a sound absorbing member, e.g., a dash silencer, a headlamp, and a tail lamp; adhesive applications of hygienic material members inclusive of a disposable diaper, a women sanitary napkin, a nonwoven fabric, and a polyethylene-made film; packaging materials, such as a heat seal packaging film; hot melt adhesive sheets for clothing; adhesive or sealing applications inclusive of a building member, e.g., a wall paper, a carpet, a tile, a plywood panel, and a thatching material, and a building material, e.g., an external wall and a heat-insulating material; box making/sealing applications inclusive of a corrugated cardboard box and a carton case; pleating and frame fixing applications of an air filter of an air conditioner, an air cleaner, etc.; surface protective film applications (for example, a resin for binder layer positioning between a substrate and a pressure-sensitive adhesive layer and a resin for pressure-sensitive adhesive layer); medical devices, such as a surgical drape; food trays; pressure-sensitive adhesive products, such as a tape and a label; resins for adhesive layer of a laminate; electrical appliances, such as a liquid crystal display; adhesives for bookbinding; adhesives for woodworking; asphalt-modifying agents for paved road; anti-slip materials of a mat, such as a floor mat and a bath mat; packaging adhesives inclusive of straw attachment of a beverage pack; resins for heat seal layer, such as a heat seal packaging film; and so on.

EXAMPLES

The present invention is hereunder specifically described by reference to Examples, but it should be construed that the present invention is by no means limited by these Examples. Each of the components used in the Examples and Comparative Examples is as follows.

<Olefin-based Polymer (a)>

Olefin-based polymers described below were used.

Olefin-based polymer (a)-1:

Propylene homopolymer (RT2180, manufactured by REXtac LLC; a poly-α-olefin having an amount of heat of crystal fusion (ΔH) of 23.7 J/g)

Olefin-based polymer (a)-2:

Ethylene-propylene copolymer (RT2280, manufactured by REXtac LLC; a poly-α-olefin that is a low ethylene copolymer, having an amount of heat of crystal fusion (ΔH) of 16.0 J/g)

Olefin-based polymer (a)-3:

Ethylene-propylene copolymer (RT2585, manufactured by REXtac LLC; a poly-α-olefin that is a high ethylene copolymer, having an amount of heat of crystal fusion (ΔH) of 6.8 J/g)

Olefin-based polymer (a)-4:

Propylene-1-butene random copolymer (RT2780, manufactured by REXtac LLC; a poly-α-olefin having an amount of heat of crystal fusion (ΔH) of less than 4.7 J/g)

Olefin-based polymer (a)-5;

Ethylene-propylene copolymer (Vistamaxx 3588FL, manufactured by Exxon Mobil Corporation; a polyolefin elastomer that is an ethylene copolymer having an ethylene content of 4% by mass, having an amount of heat of crystal fusion (ΔH) of 51.7 J/g)

<Hydrogenated Block Copolymer (b)>

Hydrogenated block copolymer (b)-1:

Hydrogenated block copolymer produced in the following Production Example 1

Hydrogenated block copolymer (b)-2:

Hydrogenated block copolymer produced in the following Production Example 2

Hydrogenated block copolymer (b)-3:

Hydrogenated block copolymer produced in the following Production Example 3

Hydrogenated block copolymer (b)-4:

Hydrogenated block copolymer produced in the following Production Example 4

<Comparative Hydrogenated Block Copolymer (x)>

Hydrogenated block copolymer (x)-1:

Hydrogenated block copolymer produced in the following Comparative Production Example 1

Hydrogenated block copolymer (x)-2:

Hydrogenated block copolymer produced in the following Comparative Production Example 2

Hydrogenated block copolymer (x)-3:

Hydrogenated block copolymer produced in the following Comparative Production Example 3

Production Example 1

Production of Hydrogenated Block Copolymer (b)-1

A dry nitrogen-purged pressure tight vessel was charged with cyclohexane and styrene (A1). To this solution, sec-butyllithium (10% by mass, a cyclohexane solution) was added and polymerized at 60° C. for 1 hour. Subsequently, tetrahydrofuran was added to this reaction mixture; then, a mixture of isoprene and butadiene was added to undergo polymerization for 2 hours; and styrene (A2) was further added to undergo polymerization for 1 hour, to give a reaction liquid containing a triblock copolymer of polystyrene-poly(isoprene/butadiene)-polystyrene. The use amounts of the raw materials used for the aforementioned reaction are shown in Table 1-1.

To this reaction liquid, a Ziegler-based hydrogenation catalyst formed from nickel octylate and trimethylaluminum was added in a hydrogen atmosphere to undergo a reaction for 5 hours under a condition at a hydrogen pressure of 1.0 MPa and 80° C. Subsequently, after allowing the reaction liquid to stand for cooling and pressure discharge, the catalyst was removed by washing with water and then dried in vacuo to give a hydrogenated product of a polystyrene-poly(isoprene/butadiene)-polystyrene triblock copolymer (hereinafter also referred to as "hydrogenated block copolymer (b)-1"). The resulting hydrogenated block copolymer (b)-1 was analyzed and evaluated for physical properties according to the methods as mentioned later. The results are shown in Table 1-1.

Production Example 2 and Comparative Production Examples 1 to 2

Production of Hydrogenated Block Copolymer (b)-2 and Comparative Hydrogenated Block Copolymers (x)-1 and (x)-2

A hydrogenated block copolymer (b)-2 and comparative hydrogenated block copolymers (x)-1 and (x)-2 were produced in the same manner as in Production Example 1, except for changing the use amounts of the raw materials to those described in Table 1-1. The resulting hydrogenated block copolymer (b)-2 and comparative hydrogenated block copolymers (x)-1 and (x)-2 were analyzed and evaluated for physical properties according to the methods as mentioned later. The results are shown in Table 1-1.

Production Examples 3 and 4

Production of Hydrogenated Block Copolymers (b-3) and (b-4)

Hydrogenated block copolymers (b)-3 and (b)-4 were produced in the same manner as in Production Example 1, except for changing the use amounts of the raw materials to those described in Table 1-2. The resulting hydrogenated block copolymers (b)⁻3 and (b) −4 were analyzed and evaluated for physical properties according to the methods as mentioned later. The results are shown in Table 1-2.

Comparative Example 3

Production of Comparative Hydrogenated Block Copolymer (x)-3

A comparative hydrogenated block copolymer (x)-3 was produced in the same manner as in Production Example 1, except for using N,N,N',N'-tetramethylethylenediamine in place of the tetrahydrofuran and changing the use amounts of the raw materials to those described in Table 1-3. The resulting comparative hydrogenated block copolymer (x)-3 was analyzed and evaluated for physical properties according to the methods as mentioned later. The results are shown in Table 1-3.

[Measurement Method of Physical Properties of Hydrogenated Block Copolymer (b) and Comparative Hydrogenated Block Copolymer (x)]

(1) Peak Top Molecular Weight (Mp) and Molecular Weight Distribution (Mw/Mn)

The peak top molecular weight (Mp) as expressed in terms of polystyrene of each of the copolymers, the polymer blocks (A), and the polymer blocks (B) was determined by the gel permeation chromatography (GPC) measurement under the following condition. In addition, the molecular weight distribution (Mw/Mn) was calculated from the weight average molecular weight (Mw) and the number average molecular weight (Mn) determined as a molecular weight as expressed in terms of standard polystyrene by the gel permeation chromatography (GPC).

(GPC Measuring Apparatus and Measuring Condition)
Apparatus: GPC apparatus "HLC-8320" (manufactured by Tosoh Corporation)
Separation columns: Two columns "TSKgel Super HZ4000" (manufactured by Tosoh Corporation) were serially concatenated.
Eluent: Tetrahydrofuran Eluent flow rate: 0.35 mL/min
Sample concentration: 5 mg/10 mL
Column temperature: 40° C.
Detector: Differential refractive index (RI) detector
Calibration curve: Prepared using standard polystyrene (2) Contents of Polymer Block (A) and Polymer Block (B)

The block copolymer before hydrogenation was dissolved in $CDCl_3$ and measured for a $^1H$-NMR spectrum with an apparatus: "ULTRASHIELD 400 PLUS" (manufactured by Bruker Corporation) at a measuring temperature of 50° C., and the contents of the polymer block (A) and the polymer block (B) were calculated from a ratio of a peak area derived from styrene and a peak area derived from isoprene and butadiene.

(3) Hydrogenation Rate of Copolymer

The block copolymer before and after hydrogenation was dissolved in $CDCl_3$ and measured for a $^1H$-NMR spectrum with an apparatus: "ULTRASHIELD 400 PLUS" (manufactured by Bruker Corporation) at a measuring temperature of 50° C., and the hydrogenation rate was determined from a reduction rate in a peak area ratio derived from a carbon-carbon double bond of each of the conjugated diene polymer block before and after hydrogenation.

(4) Proportion of Vinyl Bond Amount of Polymer Block (B)

The block copolymer before hydrogenation was dissolved in $CDCl_3$ and measured for a $^1H$-NMR spectrum with an apparatus: "ULTRASHIELD 400 PLUS" (manufactured by Bruker Corporation) at a measuring temperature of 50° C., and the proportion of the vinyl bond amount (total content of the 3,4-bond unit and the 1,2-bond unit) was calculated from a ratio of the total peak area of structural units derived from isoprene and butadiene and the total peak area of the 3,4-bond unit and the 1,2-bond unit in the isoprene structural unit and the 1,2-bond unit in the butadiene structural unit.

(5) Glass Transition Temperature

Using a differential scanning calorimeter "DSC 6200", manufactured by Seiko Instruments Inc., the temperature was raised at a temperature rise rate of 10° C./min from −120° C. to 100° C. in conformity with JIS K7121:2012, and the glass transition temperature was determined from the resulting DSC curve. In the case of the hydrogenated block copolymer (b) and the comparative hydrogenated block copolymer (x), the glass transition temperature derived from the polymer block (B) is observed.

(6) Melt Flow Rate (MFR)

Using a melt indexer (TAKARA L241, manufacture by Technol Seven Co., Ltd.), the melt flow rate was measured under a condition at a temperature of 230° C. and a load of 2.16 kg in conformity with JIS K7210-1:2014.

(7) Solubility Parameter (SP Value) of Polymer Block (B)

The solubility parameter (SP value) of the polymer (B) was calculated on a basis of the structure of the polymer block (B) by the Hoy method described in "Properties of Polymers (4th Edition): D. W. van Krevelen, Klaas to Nijenhuis; Elsevier Science, 2009".

TABLE 1-1

| | | Production Example 1 (b)-1 | Production Example 2 (b)-2 | Comparative Production Example 1 (x)-1 | Comparative Production Example 2 (x)-2 |
|---|---|---|---|---|---|
| Use amount (kg) | Cyclohexane | 50.0 | 50.0 | 50.0 | 50.0 |
| | sec-Butyllithium (10% by mass, cyclohexane solution) | 0.0427 | 0.0433 | 0.163 | 0.0617 |
| | Tetrahydrofuran | 0.288 | 0.288 | 0 | 0.112 |
| | Styrene (A1) | 0.352 | 0.264 | 1.32 | 0.529 |
| | Styrene (A2) | 0.352 | 0.793 | 1.32 | 0.529 |
| | Isoprene | 4.46 | 3.82 | 6.17 | 0.00 |
| | Butadiene | 3.65 | 3.94 | 0.00 | 7.76 |
| Physical properties | Polymer block sequence | A1-B-A2 | A1-B-A2 | A1-B-A2 | A1-B-A2 |
| | Peak top molecular weight (Mp) | 166,000 | 165,000 | 52,000 | 137,000 |
| | Mp(A1) | 5,000 | 3,700 | 4,900 | 5,200 |
| | Mp(A2) | 5,000 | 11,100 | 4,900 | 5,200 |
| | Mp(A1)/Mp(A2) | 1/1 | 1/3 | 1/1 | 1/1 |
| | Weight average molecular weight (Mw) | 162,000 | 163,000 | 51,500 | 135,000 |
| | Number average molecular weight (Mn) | 159,000 | 160,000 | 50,700 | 131,000 |
| | Molecular weight distribution (Mw/Mn) | 1.02 | 1.02 | 1.02 | 1.03 |
| | Content of polymer block (A) (% by mass) | 8.0 | 12.0 | 30.0 | 12.0 |
| | Content of polymer block (B) (% by mass) | 92.0 | 88.0 | 70.0 | 88.0 |
| | Hydrogenation rate (mol %) | 92 | 92 | 99 | 99 |

TABLE 1-1-continued

|  | Production Example 1 (b)-1 | Production Example 2 (b)-2 | Comparative Production Example 1 (x)-1 | Comparative Production Example 2 (x)-2 |
|---|---|---|---|---|
| Proportion of vinyl bond amount of polymer block (B) (mol %) | 60.0 | 62.0 | 5.0 | 38.0 |
| Glass transition temperature (° C.) | −30 | −32 | −56 | −53 |
| MFR (230° C., 2.16 kg) (g/10 min) | 19 | 2 | 70 | 8 |
| SP value of polymer block (B) (MPa$^{1/2}$) | 17.08 | 17.12 | 17.33 | 17.64 |

TABLE 1-2

|  |  | Production Example 3 (b)-3 | Production Example 4 (b)-4 |
|---|---|---|---|
| Use amount (kg) | Cyclohexane | 50.0 | 50.0 |
|  | sec-Butyllithium (10% by mass, cyclohexane solution) | 0.0680 | 0.0160 |
|  | Tetrahydrofuran | 0.288 | 0.288 |
|  | Styrene (A1) | 0.905 | 0.129 |
|  | Styrene (A2) | 0.905 | 0.129 |
|  | Isoprene | 7.00 | 3.18 |
|  | Butadiene | 0.00 | 2.98 |
| Physical properties | Polymer block sequence | A1-B-A2 | A1-B-A2 |
|  | Peak top molecular weight (Mp) | 110,000 | 354,000 |
|  | Mp(A1) | 8,300 | 5,000 |
|  | Mp(A2) | 8,300 | 5,000 |
|  | Mp(A1)/Mp(A2) | 1/1 | 1/1 |
|  | Weight average molecular weight (Mw) | 106,000 | 296,000 |
|  | Number average molecular weight (Mn) | 102,000 | 252,000 |
|  | Molecular weight distribution (Mw/Mn) | 1.04 | 1.18 |
|  | Content of polymer block (A) (% by mass) | 20.8 | 4.0 |
|  | Content of polymer block (B) (% by mass) | 79.2 | 96.0 |
|  | Hydrogenation rate (mol %) | 90 | 95 |
|  | Proportion of vinyl bond amount of polymer block (B) (mol %) | 62.3 | 62.2 |
|  | Glass transition temperature (° C.) | −14 | −30 |
|  | MFR (230° C., 2.16 kg) (g/10 min) | 4 | 1.4 |
|  | SP value of polymer block (B) (MPa$^{1/2}$) | 16.80 | 17.09 |

TABLE 1-3

|  |  | Comparative Production Example 3 (x)-3 |
|---|---|---|
| Use amount (kg) | Cyclohexane | 50.0 |
|  | sec-Butyllithium (10% by mass, cyclohexane solution) | 0.0737 |
|  | N,N,N',N'-tetramethylethylenediamine | 0.0100 |
|  | Styrene (A1) | 0.800 |
|  | Styrene (A2) | 0.800 |
|  | Isoprene | 0 |
|  | Butadiene | 7.26 |
| Physical properties | Polymer block sequence | A1-B-A2 |
|  | Peak top molecular weight (Mp) | 129,000 |
|  | Mp(A1) | 6,600 |
|  | Mp(A2) | 6,600 |
|  | Mp(A1)/Mp(A2) | 1/1 |
|  | Weight average molecular weight (Mw) | 127,000 |
|  | Number average molecular weight (Mn) | 120,000 |
|  | Molecular weight distribution (Mw/Mn) | 1.06 |
|  | Content of polymer block (A) (% by mass) | 18.0 |
|  | Content of polymer block (B) (% by mass) | 82.0 |
|  | Hydrogenation rate (mol %) | 99 |
|  | Proportion of vinyl bond amount of polymer block (B) (mol %) | 76.0 |
|  | Glass transition temperature (° C.) | −42 |
|  | MFR (230° C., 2.16 kg) (g/10 min) | 18 |
|  | SP value of polymer block (B) (MPa$^{1/2}$) | 17.26 |

Examples 1 to 16 and Comparative Examples 2, 3, and 8

Using a mixer (Plastograph EC, manufactured by Brabender GmbH & Co. KG.), respective components of the kinds and compounding amounts shown in Tables 3 to 6 were melt-kneaded at a temperature of 170° C. and a rotation number of 80 rpm for 30 minutes, to give thermoplastic resin compositions. The resulting thermoplastic resin compositions were each evaluated for physical properties according to the following methods. The results are shown in Tables 3 to 6. In Tables 3 to 6, the blank column expresses "not compounded".

Comparative Examples 1 and 4 to 7

The olefin-based polymers (a) used in Comparative Examples 1 and 4 to 7 were each evaluated for physical properties according to the following methods. The results are shown in Tables 3, 4, and 6.

<Preparation of Sheets of Thermoplastic Resin Compositions>

Examples 1 to 5, Examples 8 to 10, Example 13, Example 14, Comparative Examples 1 to 4, and Comparative Example 8

The thermoplastic resin compositions were each heat-pressed under a condition at a temperature of 180° C. and a pressure of 10 MPa for a pressing time of 2 minutes, to prepare sheets having a thickness of 1 mm, 300 μm, and 100 μm, respectively.

Example 6, Example 7, Example 11, Example 12, Example 15, Example 16, and Comparative Examples 5 to 7

The thermoplastic resin compositions were each heat-pressed under a condition at a temperature of 140° C. and a pressure of 10 MPa for a pressing time of 2 minutes, to prepare sheets having a thickness of 1 mm, 300 μm, and 100 μm, respectively.

<Evaluation of Physical Properties of Thermoplastic Resin Composition>

(1) Loss Modulus (G")

A specimen having been cut out in a disc form having a diameter of 8 mm and a thickness of 1 mm from the sheet of the thermoplastic resin composition (thickness: 1 mm) as obtained in the aforementioned method was measured for dynamic viscoelasticity using an ARES-G2 rheometer (manufactured by TA Instruments, Inc.), to determine the number of maximum peaks and a maximum peak temperature of a loss modulus (G") appearing in a temperature range of −70° C. to 0° C.

Figure 1:
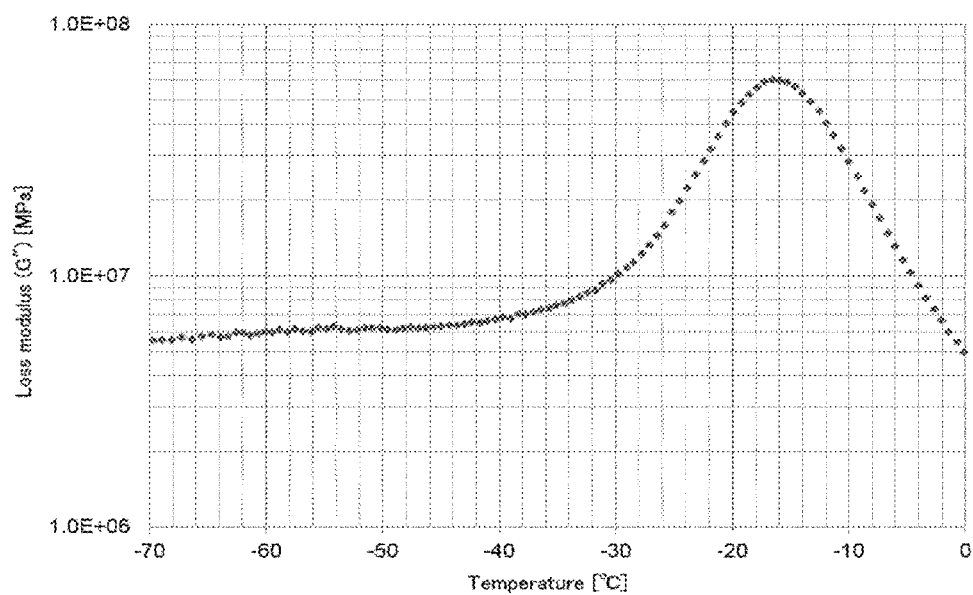
FIG. 1 is a dynamic viscoelasticity measurement chart of a thermoplastic resin composition sheet of Example 1.
Figure 2:
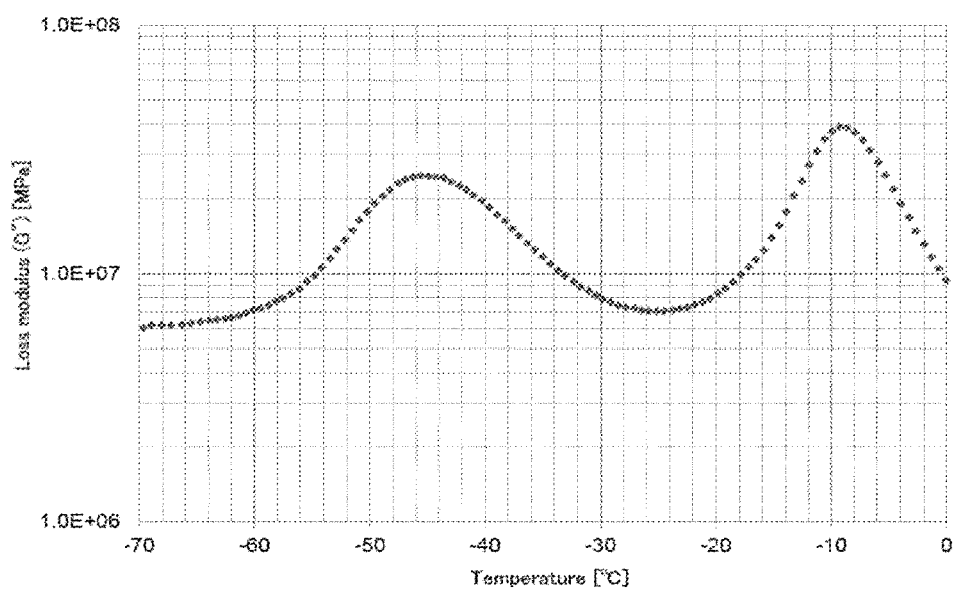
FIG. 2 is a dynamic viscoelasticity measurement chart of a thermoplastic resin composition sheet of Comparative Example 2.

Dynamic viscoelasticity measurement charts of Example 1 and Comparative Example 2 are shown in FIG. 1 and FIG. 2, respectively.

(Dynamic Viscoelastometer and Measuring Condition)

Parallel plate: Diameter, 8 mm

Vibration mode: Torsional vibration

Strain amount: 0.1%

Frequency: 1 Hz

Measuring temperature: −70 to 0° C.

Temperature rise rate: 3° C./min (2) Crystallization Temperature, Glass Transition Temperature, Melting Point, and Amount of Heat of Crystal Fusion (ΔH)

Using a differential scanning calorimeter "DSC 6200", manufactured by Seiko Instruments Inc., the measurement was conducted in conformity with JIS K7121:2012 and JIS K7122:2012 while changing the temperature in the order of the following heating step 1, cooling step, and heating step 2. In Examples 1 to 6, Examples 8 to 11, Example 13 to 16, Comparative Examples 1 to 5, Comparative Example 7, and Comparative Example 8, the crystallization temperature was determined from the DSC curve obtained in the cooling step, and in Example 7, Example 12, and Comparative Example 6, the crystallization temperature was determined from the DSC curve obtained in the heating step 2. In addition, the glass transition temperature, the melting point, and the amount of heat of crystal fusion (ΔH) were obtained from the DSC curve obtained in the heating step 2.

Heating Step 1:
Heated from 30° C. to 180° C. at a heating rate of 10° C./min

Cooling Step:
Cooled from 180° C. to −70° C. at a cooling rate of 10° C./min

Heating step 2:
Heated from −70° C. to 180° C. at a heating rate of 10° C./min (3) Tensile Hysteresis Loss, M100

A specimen of 25 mm×150 mm×300 μm in thickness was cut out from the sheet of the thermoplastic resin composition (thickness: 300 μm) as obtained in the aforementioned method, and an operation of stretching to a strain of 100% at a distance between chucks of 40 mm and at a rate of 300 mm/min using a tensile tester (Model 3345, manufactured by Instron Tool Works, Inc.) and immediately thereafter, returning to the original state at the same rate was repeatedly conducted twice. According to the calculation method described in 11.2.4 of JIS K7312:1996, a hysteresis loss determined from the first stress-strain curve was defined as a hysteresis loss-1, and a hysteresis loss determined from the second stress-strain curve was defined as a hysteresis loss-2. In addition, the stress at a strain of 100% in the first stress-strain curve was defined as M100. The lower the numerical value of the hysteresis loss, the more excellent the stretchability is.

(4) Haze

The haze of the sheet of the thermoplastic resin composition (thickness: 1 mm) as obtained in the aforementioned method was determined using a haze meter (HR-100, manufacture by Murakami Color Research Laboratory Co., Ltd.) in conformity with JIS K7136:2000.

(5) Adhesive Force

A specimen of 25 mm×150 mm×100 μm in thickness was cut out from the sheet of the thermoplastic resin composition (thickness: 100 μm) as obtained in the aforementioned method and sandwiched by two clothes (manufactured by UNIQLO CO., LTD., a color T-shirt, cotton: 66%, polyester: 34%), followed by adhesion under the following adhesion condition.

(Adhesion Condition)

Examples 1 to 3, Example 8, Example 9, Example 13, Example 14, Comparative Examples 1 to 3, and Comparative Example 8: 145° C., 30 seconds, 0.06 MPa Example 4, Example 5, Example 10, and Comparative Example 4: 135° C., 30 seconds, 0.06 MPa Example 6, Example 11, and Comparative Example 5: 105° C., 30 seconds, 0.06 MPa Example 7, Example 12, and Comparative Example 6: 85° C., 30 seconds, 0.06 MPa Example 15, Example 16, and Comparative Example 7: 158° C., 30 seconds, 0.06 MPa With respect to the resulting laminates composed of (cloth)/(thermoplastic resin composition)/(cloth), the adhesive force was determined by measuring a peel strength using a T-type peeling test in conformity with JIS L1086: 2013. In addition, the peeled surface of the specimen after the peeling test was visually observed, and the state of the peeled surface was judged according to the judgement criteria shown in the following Table 2. The case where on the occasion of the peel test, the cloth was ruptured was determined as "substrate failure". The "substrate failure" means that the laminate is adhered more strongly than the strength of the adherend.

TABLE 2

| State of peeled surface | Judgement |
|---|---|
| In an area of 90% or more of the peeled surface, the layer of the thermoplastic resin composition causes cohesive failure and is peeled. | Cohesive failure 3 |
| In an area of 70% or more and less than 90% of the peeled surface, the layer of the thermoplastic resin composition causes cohesive failure and is peeled. | Cohesive failure 2 |
| In an area of 10% or more and less than 70% of the peeled surface, the layer of the thermoplastic resin composition causes cohesive failure and is peeled. | Cohesive failure 1 |
| In an area of more than 90% of the peeled surface, peeling is generated at an interface between the cloth and the layer of the thermoplastic resin composition. | Interfacial failure |

(6) Judgement Criteria of Morphology

The sheet having a thickness of 1 mm prepared by the aforementioned method was dipped in tetrahydrofuran as a solvent for 5 minutes to undergo an etching treatment, and the morphology was observed using a scanning electron microscope (SEM) (JSM-6510, manufactured by JEOL Corporation). In an observation region of 200 μm×150 μm, the case where a concave having a size of a long side of 10 μm or more is observed was judged as "immiscible", and the case where the foregoing concave is not observed was judged as "miscible".

SEM photographs of Example 1 and Comparative Example 2 are shown in FIG. 3 and FIG. 4, respectively.

(7) Scanning Probe Microscope (SPM) Observation of Thermoplastic Resin Composition A central part of the sheet having a thickness of 1 mm prepared by the aforementioned method was subjected to surface shaping under the following cross-sectional preparation condition, and after one day, the SPM observation was conducted under the following SPM measuring condition. The observation results of Example 1 and Comparative Example 2 are shown in FIG. 5 and FIG. 6, respectively.

(Cross-Sectional Preparation Condition)
Apparatus: UC-7, manufactured by Leica Camera AG
Sample•knife•atmosphere: —100° C.
Cut thickness: 150 nm
Speed: 0.3 mm/s
Knife used: Glass knife (SPM Measuring Condition)
Apparatus: Scanning probe microscope (SPM), manufactured by SII Nanotechnology Inc.
Measuring temperature: 25° C.
Measuring mode: Tapping mode
Cantilever: SI-DF20

TABLE 3

| | | | Unit | Example 1 | Example 2 | Example 3 | Comparative Example 1 | Comparative Example 2 | Comparative Example 3 |
|---|---|---|---|---|---|---|---|---|---|
| Thermoplastic resin composition | Olefin-based polymer (a) | (a)-1 | Mass parts | 75 | 75 | 90 | 100 | 75 | 75 |
| | Hydrogenated block copolymer (b) | (b)-1 | Mass parts | 25 | | 10 | | | |
| | | (b)-2 | Mass parts | | 25 | | | | |
| | Comparative hydrogenated block copolymer (x) | (x)-1 | Mass parts | | | | | 25 | |
| | | (x)-2 | Mass parts | | | | | | 25 |
| Physical properties | Number of maximum peaks of loss modulus (G") appearing in a temperature range of −70 to 0° C. | | — | 1 | 1 | 1 | 1 | 2 | 2 |
| | Maximum peak temperature-1 of loss modulus (G") | | ° C. | −15.9 | −15.2 | −10.0 | −9.3 | −9.3 | −9.3 |
| | Maximum peak temperature-2 of loss modulus (G") | | ° C. | — | — | — | — | −44.9 | −44.3 |
| | Crystallization temperature | | ° C. | 95.8 | 105.6 | 103.6 | 97.8 | 102.2 | 106.4 |
| | Glass transition temperature | | ° C. | −25.7 | −26.0 | −15.9 | −15.5 | −12.9 | −13.2 |
| | Melting point | | ° C. | 154.4 | 155.4 | 155.0 | 154.7 | 155.4 | 155.3 |
| | Amount of heat of crystal fusion (ΔH) | | J/g | 16.3 | 16.1 | 19.7 | 23.7 | 16.8 | 17.5 |
| | Hysteresis loss-1 | | % | 73.8 | 73.0 | 83.3 | 84.7 | 73.6 | 77.2 |
| | Hysteresis loss-2 | | % | 46.0 | 46.6 | 55.9 | 57.8 | 45.8 | 50.8 |
| | M100 | | MPa | 1.80 | 1.81 | 2.60 | 2.92 | 2.46 | 2.25 |
| | Haze | | % | 22.8 | 29.5 | 25.5 | 87.4 | 85.1 | 31.5 |
| | Adhesive force | | N/25 mm | 55.1 | 42.4 | 34.9 | 9.2 | 21.1 | 23.7 |
| | State of peeled surface | | — | Cohesive failure 3 | Cohesive failure 1 | Cohesive failure 2 | Cohesive failure 3 | Cohesive failure 1 | Cohesive failure 1 |
| | Morphology | | — | Miscible | Miscible | Miscible | — | Immiscible | Immiscible |

TABLE 4

| | | | Unit | Example 4 | Example 5 | Example 6 | Example 7 | Comparative Example 4 | Comparative Example 5 | Comparative Example 6 |
|---|---|---|---|---|---|---|---|---|---|---|
| Thermoplastic resin composition | Olefin-based polymer (a) | (a)-2 | Mass parts | 75 | 90 | | | 100 | | |
| | | (a)-3 | Mass parts | | | 75 | | | 100 | |
| | | (a)-4 | Mass parts | | | | 75 | | | 100 |
| | Hydrogenated block copolymer (b) | (b)-1 | Mass parts | 25 | 10 | 25 | 25 | | | |

TABLE 4-continued

| | | Unit | Example 4 | Example 5 | Example 6 | Example 7 | Comparative Example 4 | Comparative Example 5 | Comparative Example 6 |
|---|---|---|---|---|---|---|---|---|---|
| Physical properties | Number of maximum peaks of loss modulus (G″) appearing in a temperature range of −70 to 0° C. | — | 1 | 1 | 1 | 1 | 1 | 1 | 1 |
| | Maximum peak temperature-1 of loss modulus (G″) | ° C. | −19.2 | −15.2 | −30.4 | −25.2 | −15.3 | −30.4 | −17.9 |
| | Maximum peak temperature-2 of loss modulus (G″) | ° C. | — | — | — | — | — | — | — |
| | Crystallization temperature | ° C. | 87.2 | 91.1 | 63.1 | 31.2 | 86.5 | 68.3 | 27.7 |
| | Glass transition temperature | ° C. | −25.3 | −21.4 | −36.0 | −25.1 | −19.6 | −35.3 | −24.0 |
| | Melting point | ° C. | 147.3 | 147.5 | Observation impossible | Observation impossible | 147.4 | 114.8 | Observation impossible |
| | Amount of heat of crystal fusion (ΔH) | J/g | 11.0 | 14.8 | Observation impossible | Observation impossible | 16.0 | 6.8 | Less than 4.7 |
| | Hysteresis loss-1 | % | 70.6 | 78.2 | 63.8 | 69.6 | 89.6 | 89.4 | 83.7 |
| | Hysteresis loss-2 | % | 41.7 | 49.0 | 44.3 | 44.9 | 62.0 | 65.7 | 58.1 |
| | M100 | MPa | 1.24 | 1.42 | 0.33 | 0.61 | 1.26 | 0.24 | 0.54 |
| | Haze | % | 22.7 | 26.7 | 29.4 | 55.2 | 54.3 | 57.2 | 25.5 |
| | Adhesive force | N/25 mm | 44.7 | 28.7 | 25.3 | 36.3 | 13.5 | 3.3 | 19.5 |
| | State of peeled surface | — | Cohesive failure 3 | Cohesive failure 1 | Cohesive failure 2 | Cohesive failure 1 | Cohesive failure 1 | Cohesive failure 2 | Cohesive failure 1 |
| | Morphology | — | Miscible | Miscible | Miscible | Miscible | | | |

TABLE 5

| | | Unit | Example 8 | Example 9 |
|---|---|---|---|---|
| Thermoplastic resin composition | Olefin-based polymer (a) (a)-1 | Mass parts | 75 | 75 |
| | Hydrogenated block copolymer (b) (b)-3 | Mass parts | 25 | |
| | (b)-4 | Mass parts | | 25 |
| Physical properties | Number of maximum peaks of loss modulus (G″) appearing in a temperature range of −70 to 0° C. | — | 1 | 1 |
| | Maximum peak temperature-1 of loss modulus (G″) | ° C. | −10.0 | −15.0 |
| | Maximum peak temperature-2 of loss modulus (G″) | ° C. | — | — |
| | Crystallization temperature | ° C. | 104.6 | 93.6 |
| | Glass transition temperature | ° C. | −17.0 | −20.9 |
| | Melting point | ° C. | 154.0 | 154.9 |
| | Amount of heat of crystal fusion (ΔH) | J/g | 19.4 | 16.8 |
| | Hysteresis loss-1 | % | 80.7 | 75.8 |
| | Hysteresis loss-2 | % | 55.7 | 46.3 |
| | M100 | MPa | 2.37 | 1.87 |
| | Haze | % | 78.6 | 19.3 |
| | Adhesive force | N/25 mm | 31.3 | 50.7 |
| | State of peeled surface | — | Cohesive failure 2 | Cohesive failure 3 |
| | Morphology | — | Miscible | Miscible |

TABLE 6

| | | Unit | Example 10 | Example 11 | Example 12 | Example 13 | Example 14 | Example 15 | Example 16 | Comparative Example 7 | Comparative Example 8 |
|---|---|---|---|---|---|---|---|---|---|---|---|
| Thermoplastic resin composition | Olefin-based polymer (a) (a)-1 | Mass parts | 75 | | | | | | | | |
| | (a)-2 | Mass parts | | 75 | | | | | | | |
| | (a)-3 | Mass parts | | | | 80 | | | | | 75 |
| | (a)-4 | Mass parts | | | | | 80 | | | | |
| | (a)-5 | Mass parts | | | 75 | | | | | | |
| | Hydrogenated block copolymer (b) (b)-1 | Mass parts | | | | | | 80 | | | |
| | (b)-4 | Mass parts | | | | | | | 80 | 100 | |
| | Comparative Hydrogenated block copolymer (x) (x)-3 | Mass parts | 25 | 25 | 25 | 20 | 20 | 20 | 20 | | 25 |
| Physical properties | Number of maximum peaks of loss modulus (G″) appearing in a temperature range of −70 to 0° C. | — | 1 | 1 | 1 | 1 | 1 | 1 | 1 | 1 | 2 |
| | Maximum peak temperature-1 of loss modulus (G″) | ° C. | −19.0 | −30.5 | −22.5 | −14.0 | −17.9 | −15.0 | −14.4 | −7.8 | −9.1 |
| | Maximum peak temperature-2 of loss modulus (G″) | ° C. | — | — | — | — | — | — | — | — | −24.9 |
| | Crystallization temperature | ° C. | 85.2 | 58.1 | 31.6 | 101.4 | 90.4 | 66.8 | 66.9 | 69.2 | 98.9 |
| | Glass transition temperature | ° C. | −24.7 | −36.3 | −33.9 | −23.3 | −24.0 | −30.4 | −29.8 | −16.7 | −10.4 |
| | Melting point | ° C. | 148.7 | Observation impossible | Observation impossible | 154.9 | 147.5 | 107.2 | 106.4 | 107.7 | 155.5 |
| | Amount of heat of crystal fusion (ΔH) | J/g | 10.8 | Observation impossible | Observation impossible | 18.9 | 14.0 | 39.0 | 44.6 | 51.7 | 13.1 |
| | Hysteresis loss-1 | % | 71.0 | 67.7 | 68.7 | 79.9 | 74.7 | 85.6 | 85.2 | 93.4 | 78.3 |
| | Hysteresis loss-2 | % | 41.2 | 51.3 | 44.6 | 51.9 | 45.9 | 58.6 | 56.6 | 64.6 | 48.1 |
| | M100 | MPa | 1.23 | 0.30 | 0.62 | 2.08 | 1.31 | 7.68 | 7.40 | 10.62 | 3.23 |
| | Haze | % | 20.0 | 17.5 | 40.6 | 23.0 | 23.1 | 32.0 | 39.4 | 46.7 | 53.1 |
| | Adhesive force | N/25 mm | 49.8 | 35.4 | 40.9 | 49.1 | 40.5 | 111.2 | 91.5 | 78.9 | 26.7 |
| | State of peeled surface | — | Cohesive failure 3 | Cohesive failure 2 | Cohesive failure 2 | Cohesive failure 3 | Cohesive failure 2 | Substrate failure | Cohesive failure 2 | Cohesive failure 2 | Cohesive failure 1 |
| | Morphology | — | Miscible | Miscible | Miscible | Miscible | Miscible | Miscible | Miscible | Miscible | Immiscible |

In Examples 1 to 3, 8, 9, and 13, it is noted that the olefin-based polymer (a)-1 and the polymer block (B) of each of the hydrogenated block copolymers (b)-1 to (b)-4 are made miscible with each other on a molecular level, and all of the stretchability, adhesiveness, and transparency are improved as compared with those in Comparative Example 1 using the olefin-based polymer (a)-1 alone. In addition, even in Comparative Examples 2, 3, and 8 in which the both are immiscible, though all of the stretchability, adhesiveness, and transparency are improved as compared with those in Comparative Example 1, it is noted that in Examples 1, 2, 8, and 9 in which the hydrogenated block copolymer (b) is contained at the same compounding ratio, the adhesiveness is significantly improved as compared with that in Comparative Examples 2, 3, and 8.

In addition, it is noted that when Examples 1, 2, and 9 in which the conjugated diene compound is a mixture of isoprene and butadiene is compared with Example 8 in which the conjugated diene compound is isoprene, Examples 1, 2, and 9 are more excellent with respect to the transparency.

In addition, in Examples 4, 5, 10, and 14, it is noted that the olefin-based polymer (a)-2 and the polymer block (B) of the hydrogenated block copolymer (b)-1 or (b)-4 are made miscible with each other on a molecular level, and all of the stretchability, adhesiveness, and transparency are improved as compared with those in Comparative Example 4 using the olefin-based polymer (a)-2 alone.

In addition, in Examples 6 and 11, it is noted that the olefin-based polymer (a)-3 and the polymer block (B) of the hydrogenated block copolymer (b)-1 or (b)-4 are made miscible with each other on a molecular level, and all of the stretchability, adhesiveness, and transparency are improved as compared with those in Comparative Example 5 using the olefin-based polymer (a)-3 alone.

In addition, in Examples 7 and 12, the olefin-based polymer (a)-4 and the polymer block (B) of the hydrogenated block copolymer (b)-1 or (b)-4 are made miscible with each other on a molecular level, and the transparency was a numerical value having no problem in a practical use, while improving the stretchability and adhesiveness as compared with those of Comparative Example 6 using the olefin-based polymer (a)-4 alone.

In addition, in Examples 15 and 16, it is noted that the olefin-based polymer (a)-5 and the polymer block (B) of the hydrogenated block copolymer (b)-1 or (b)-4 are made miscible with each other on a molecular level, and all of the stretchability, adhesiveness, and transparency are improved as compared with those in Comparative Example 7 using the olefin-based polymer (a)-5 alone.

In the light of the above, in all of the thermoplastic resin compositions of Examples 1 to 16, the olefin-based polymer (a) and the polymer block (B) of the hydrogenated block copolymer (b) are made miscible with each other, and it was demonstrated that not only the stretchability is excellent, but also high adhesive force and transparency are revealed. In particular, in the case where the conjugated diene compound is a mixture of isoprene and butadiene, it is noted that in addition to the stretchability and adhesive force, the transparency is more excellent.

The invention claimed is:

1. A thermoplastic resin composition, comprising an olefin-based polymer and a hydrogenated block copolymer, wherein
an amount of heat of crystal fusion of the olefin-based polymer measured at a heating rate of 10° C./min in differential scanning calorimetry is less than 80 J/g;
the hydrogenated block copolymer is a hydrogenated product of a block copolymer composed of a first polymer block consisting of a structural unit derived from an aromatic vinyl compound and a second polymer block consisting of a structural unit derived from a conjugated diene compound;
the content of the first polymer block in the hydrogenated block copolymer is from 1 to 60% by mass;
a proportion of a vinyl bond amount of the second polymer block is from 50 to 95 mol %;
the content of the hydrogenated block copolymer in the thermoplastic resin composition is from 1 to 30 parts by mass relative to 100 parts by mass of the total amount of the olefin-based polymer and the hydrogenated block copolymer;
the olefin-based polymer and the second polymer block of the hydrogenated block copolymer are made miscible with each other on a molecular level, and
in a temperature dispersion measurement of dynamic viscoelasticity of the thermoplastic resin composition, the number of maximum peaks of a loss modulus appearing in a temperature range of −70 to 0° C. is one.

2. The thermoplastic resin composition according to claim 1, wherein the amount of heat of crystal fusion of the olefin-based polymer is 1 J/g or more and less than 80 J/g.

3. The thermoplastic resin composition according to claim 1, wherein the olefin-based polymer is at least one olefin-based polymer selected from the group consisting of a non-crystalline or low-crystalline poly-α-olefin and a polyolefin elastomer.

4. The thermoplastic resin composition according to claim 1, wherein the olefin-based polymer is a non-crystalline or low-crystalline poly-α-olefin.

5. The thermoplastic resin composition according to claim 1, wherein a weight average molecular weight of the hydrogenated block copolymer is from 30,000 to 500,000.

6. The thermoplastic resin composition according to claim 1, wherein a molecular weight distribution of the hydrogenated block copolymer is from 1.0 to 1.5.

7. The thermoplastic resin composition according to claim 1, wherein a melt flow rate of the hydrogenated block copolymer measured under a condition at a temperature of 230° C. and a load of 2.16 kg in conformity with JIS K7210-1:2014 is from 0.1 to 90 g/10 min.

8. The thermoplastic resin composition according to claim 1, wherein the content of the first polymer block in the hydrogenated block copolymer is from 5 to 9% by mass.

9. The thermoplastic resin composition according to claim 1, wherein the second polymer block is a polymer block consisting of a structural unit derived from a mixture of isoprene and butadiene, and a mixing ratio of isoprene to butadiene [isoprene/butadiene] (molar ratio) is from 10/90 to 90/10.

10. The thermoplastic resin composition according to claim 1, further comprising a tackifier.

11. A hot melt adhesive comprising the thermoplastic resin composition according to claim 1.

12. An automobile member, comprising the hot melt adhesive according to claim 11.

13. A hygienic material member, comprising the hot melt adhesive according to claim 11.

14. The thermoplastic resin composition according to claim 1, wherein the content of the polymer block (A) in the hydrogenated block copolymer (b) is from 3 to 20% by mass.

15. The thermoplastic resin composition according to claim 1, wherein the content of the polymer block (A) in the hydrogenated block copolymer (b) is from 3 to 15% by mass.

16. The thermoplastic resin composition according to claim 1, wherein the content of the polymer block (A) in the hydrogenated block copolymer (b) is from 3 to 9% by mass.

* * * * *